(12) United States Patent
Greener

(10) Patent No.: US 11,471,333 B2
(45) Date of Patent: Oct. 18, 2022

(54) NEGATIVE PRESSURE WOUND THERAPY APPARATUS

(71) Applicant: T.J.Smith and Nephew, Limited, Hull (GB)

(72) Inventor: Bryan Greener, York (GB)

(73) Assignee: T.J.Smith and Nephew, Limited, Hull (GB)

( * ) Notice: Subject to any disclaimer, the term of this patent is extended or adjusted under 35 U.S.C. 154(b) by 136 days.

(21) Appl. No.: 16/622,207

(22) PCT Filed: Jun. 11, 2018

(86) PCT No.: PCT/EP2018/065396
§ 371 (c)(1),
(2) Date: Dec. 12, 2019

(87) PCT Pub. No.: WO2018/229008
PCT Pub. Date: Dec. 20, 2018

(65) Prior Publication Data
US 2020/0107965 A1 Apr. 9, 2020

Related U.S. Application Data

(60) Provisional application No. 62/519,762, filed on Jun. 14, 2017.

(51) Int. Cl.
*A61F 13/00* (2006.01)
*A61F 13/02* (2006.01)

(52) U.S. Cl.
CPC ...... *A61F 13/00068* (2013.01); *A61F 13/022* (2013.01); *A61F 13/0209* (2013.01); *A61F 13/0243* (2013.01); *A61F 13/0246* (2013.01)

(58) Field of Classification Search
CPC .......... A61F 13/00068; A61F 13/0209; A61F 13/022; A61F 13/0243; A61F 13/0246;
(Continued)

(56) References Cited

U.S. PATENT DOCUMENTS

| 3,972,328 A | 8/1976 | Chen |
| 4,029,598 A | 6/1977 | Neisius et al. |

(Continued)

FOREIGN PATENT DOCUMENTS

| DE | 3443101 A1 | 5/1986 |
| EP | 0340018 A2 | 11/1989 |

(Continued)

OTHER PUBLICATIONS

Definition of "Score" by Merriam-Webster On-Line Dictionary, https://www.merriam-webster.com/dictionary/score (Year: 2021).*

(Continued)

*Primary Examiner* — Andrew J Mensh
(74) *Attorney, Agent, or Firm* — Knobbe, Martens, Olson & Bear, LLP

(57) ABSTRACT

Disclosed embodiments relate to apparatuses and methods for wound treatment. In certain embodiments, a negative pressure wound therapy apparatus can include a wound dressing with a spacer layer separated from the absorbent layer by intermediate layers or drapes. The wound dressing can include a first portion comprising a wound contact or tissue contact layer, a first spacer layer, and a first backing layer comprising a first aperture. The spacer layer can be positioned between the contact layer and the first backing layer. The dressing can have a second portion comprising an intermediate drape with a second aperture, an absorbent layer, and a second backing layer. The absorbent layer is positioned between the intermediate drape and the second backing layer. The first aperture and the second aperture are configured to be sealed and allow fluid communication between the first portion and the second portion of the wound dressing.

25 Claims, 15 Drawing Sheets

(58) Field of Classification Search
CPC .............. A61F 13/0216; A61M 1/90; A61M 2205/7536; A61M 1/784
USPC ........................................................ 604/543
See application file for complete search history.

(56) References Cited

U.S. PATENT DOCUMENTS

| | | | |
|---|---|---|---|
| 4,499,896 A * | | 2/1985 | Heinecke .......... A61F 13/00063 602/57 |
| 4,728,499 A | | 3/1988 | Fehder |
| 4,813,942 A | | 3/1989 | Alvarez |
| 5,056,510 A | | 10/1991 | Gilman |
| 5,181,905 A | | 1/1993 | Flam |
| 5,238,732 A | | 8/1993 | Krishnan |
| 5,549,584 A | | 8/1996 | Gross |
| 5,707,499 A | | 1/1998 | Joshi et al. |
| 5,730,736 A | | 3/1998 | Sawers et al. |
| 5,759,570 A | | 6/1998 | Arnold |
| 5,852,126 A | | 12/1998 | Barnard et al. |
| 6,071,267 A | | 6/2000 | Zamierowski |
| 6,626,891 B2 | | 9/2003 | Ohmstede |
| 6,685,681 B2 | | 2/2004 | Lockwood et al. |
| 6,752,794 B2 | | 6/2004 | Lockwood et al. |
| 6,936,037 B2 | | 8/2005 | Bubb et al. |
| 6,951,553 B2 | | 10/2005 | Bubb et al. |
| 6,979,324 B2 | | 12/2005 | Bybordi et al. |
| 7,070,584 B2 | | 7/2006 | Johnson et al. |
| 7,108,683 B2 | | 9/2006 | Zamierowski |
| 7,216,651 B2 | | 5/2007 | Argenta et al. |
| 7,361,184 B2 | | 4/2008 | Joshi |
| 7,605,298 B2 | | 10/2009 | Bechert et al. |
| 7,615,036 B2 | | 11/2009 | Joshi et al. |
| 7,622,629 B2 | | 11/2009 | Aali |
| 7,625,362 B2 | | 12/2009 | Boehringer et al. |
| 7,700,819 B2 | | 4/2010 | Ambrosio et al. |
| 7,718,249 B2 | | 5/2010 | Russell et al. |
| 7,722,582 B2 | | 5/2010 | Lina et al. |
| 7,749,531 B2 | | 7/2010 | Booher |
| 7,759,537 B2 | | 7/2010 | Bishop et al. |
| 7,759,539 B2 | | 7/2010 | Shaw et al. |
| 7,775,998 B2 | | 8/2010 | Riesinger |
| 7,811,269 B2 | | 10/2010 | Boynton et al. |
| 7,910,791 B2 | | 3/2011 | Coffey |
| 7,922,703 B2 | | 4/2011 | Riesinger |
| 7,959,624 B2 | | 6/2011 | Riesinger |
| 7,976,519 B2 | | 7/2011 | Bubb et al. |
| 8,062,331 B2 | | 11/2011 | Zamierowski |
| 8,152,785 B2 | | 4/2012 | Vitaris |
| 8,235,972 B2 | | 8/2012 | Adahan |
| 8,241,261 B2 | | 8/2012 | Randolph et al. |
| 8,303,552 B2 | | 11/2012 | Weston |
| 8,372,049 B2 | | 2/2013 | Jaeb et al. |
| 8,372,050 B2 | | 2/2013 | Jaeb et al. |
| 8,425,478 B2 | | 4/2013 | Olson |
| 8,513,481 B2 | | 8/2013 | Gergely et al. |
| 8,540,688 B2 | | 9/2013 | Eckstein et al. |
| 8,545,466 B2 | | 10/2013 | Andresen et al. |
| 8,568,386 B2 | | 10/2013 | Malhi |
| 8,628,505 B2 | | 1/2014 | Weston |
| 8,641,691 B2 | | 2/2014 | Fink et al. |
| 8,663,198 B2 | | 3/2014 | Buan et al. |
| 8,795,243 B2 | | 8/2014 | Weston |
| 8,795,800 B2 | | 8/2014 | Evans |
| 9,067,003 B2 | | 6/2015 | Buan et al. |
| 9,127,665 B2 | | 9/2015 | Locke et al. |
| 9,220,822 B2 | | 12/2015 | Hartwell |
| 9,283,118 B2 | | 3/2016 | Locke et al. |
| 9,302,033 B2 | | 4/2016 | Riesinger |
| 9,375,521 B2 | | 6/2016 | Hudspeth et al. |
| 9,381,283 B2 | | 7/2016 | Adams et al. |
| 9,421,309 B2 | | 8/2016 | Robinson et al. |
| 9,427,505 B2 | | 8/2016 | Askem et al. |
| 9,452,248 B2 | | 9/2016 | Blott et al. |
| 9,629,986 B2 | | 4/2017 | Patel et al. |
| 9,681,993 B2 | | 6/2017 | Wu et al. |
| 9,682,179 B2 | | 6/2017 | May |
| 9,795,725 B2 | | 10/2017 | Joshi et al. |
| 9,829,471 B2 | | 11/2017 | Hammond et al. |
| 9,844,473 B2 | | 12/2017 | Blott et al. |
| 9,962,474 B2 | | 5/2018 | Greener |
| 10,016,545 B2 | | 7/2018 | Vitaris et al. |
| 10,046,096 B2 | | 8/2018 | Askem et al. |
| 10,105,471 B2 | | 10/2018 | Weston |
| 10,149,931 B2 | | 12/2018 | Robinson et al. |
| 10,188,555 B2 | | 1/2019 | Vitaris et al. |
| 10,201,644 B2 | | 2/2019 | Haggstrom et al. |
| 10,328,188 B2 | | 6/2019 | Deutsch et al. |
| 11,058,587 B2 | | 7/2021 | Adie et al. |
| 2003/0125646 A1 | | 7/2003 | Whitlock |
| 2004/0030304 A1 * | | 2/2004 | Hunt ........................ A61L 15/24 604/317 |
| 2004/0057855 A1 | | 3/2004 | Gerlach et al. |
| 2006/0009744 A1 | | 1/2006 | Erdman et al. |
| 2007/0040454 A1 | | 2/2007 | Freudenberger et al. |
| 2007/0225663 A1 | | 9/2007 | Watt et al. |
| 2008/0031748 A1 | | 2/2008 | Ihle et al. |
| 2008/0132821 A1 | | 6/2008 | Propp et al. |
| 2009/0125004 A1 | | 5/2009 | Shen et al. |
| 2009/0157024 A1 | | 6/2009 | Song |
| 2009/0234306 A1 | | 9/2009 | Vitaris |
| 2009/0299306 A1 | | 12/2009 | Buan |
| 2010/0125258 A1 | | 5/2010 | Coulthard et al. |
| 2010/0185163 A1 * | | 7/2010 | Heagle ............. A61F 13/00068 604/290 |
| 2010/0259406 A1 | | 10/2010 | Caso et al. |
| 2010/0318052 A1 | | 12/2010 | Ha et al. |
| 2011/0004172 A1 | | 1/2011 | Eckstein et al. |
| 2011/0224631 A1 | | 9/2011 | Simmons et al. |
| 2012/0051945 A1 | | 3/2012 | Orndorff et al. |
| 2012/0109083 A1 * | | 5/2012 | Coulthard ........... A61F 13/0216 604/319 |
| 2013/0066285 A1 | | 3/2013 | Locke et al. |
| 2013/0066289 A1 | | 3/2013 | Song et al. |
| 2013/0090616 A1 | | 4/2013 | Neubauer |
| 2013/0131616 A1 | | 5/2013 | Locke |
| 2013/0138054 A1 | | 5/2013 | Fleischmann |
| 2013/0144227 A1 | | 6/2013 | Locke et al. |
| 2013/0165878 A1 | | 6/2013 | Heagle |
| 2013/0296762 A1 | | 11/2013 | Toth |
| 2013/0302545 A1 | | 11/2013 | Schnelker et al. |
| 2014/0114268 A1 | | 4/2014 | Auguste et al. |
| 2014/0200533 A1 | | 7/2014 | Whyte et al. |
| 2014/0316359 A1 * | | 10/2014 | Collinson .......... A61F 13/00068 604/319 |
| 2015/0032035 A1 | | 1/2015 | Banwell et al. |
| 2015/0119831 A1 | | 4/2015 | Robinson et al. |
| 2015/0119832 A1 | | 4/2015 | Locke |
| 2015/0119833 A1 | | 4/2015 | Coulthard et al. |
| 2015/0141941 A1 * | | 5/2015 | Allen ................. A61F 13/00068 604/319 |
| 2015/0182677 A1 * | | 7/2015 | Collinson .......... A61F 13/00042 604/319 |
| 2015/0216732 A1 * | | 8/2015 | Hartwell ........... A61F 13/00987 604/319 |
| 2015/0216733 A1 * | | 8/2015 | Allen ................. A61F 13/00059 604/319 |
| 2016/0000611 A1 | | 1/2016 | Niederauer et al. |
| 2016/0120706 A1 * | | 5/2016 | Collinson ............ A61F 13/0253 604/319 |
| 2016/0144084 A1 * | | 5/2016 | Collinson .......... A61F 13/00068 604/319 |
| 2016/0298620 A1 | | 10/2016 | Cordoba et al. |
| 2017/0128642 A1 | | 5/2017 | Buan |
| 2017/0181897 A1 | | 6/2017 | Hartwell |
| 2017/0368239 A1 | | 12/2017 | Askem et al. |
| 2018/0133378 A1 | | 5/2018 | Askem et al. |
| 2018/0318476 A1 | | 11/2018 | Askem et al. |
| 2019/0133828 A1 | | 5/2019 | Kazala, Jr. et al. |
| 2019/0133830 A1 * | | 5/2019 | Bishop .................... A61M 1/90 |

(56) References Cited

U.S. PATENT DOCUMENTS

| | | | |
|---|---|---|---|
| 2020/0121833 A9 | 4/2020 | Askem et al. | |
| 2020/0139023 A1 | 5/2020 | Haggstrom et al. | |

FOREIGN PATENT DOCUMENTS

| | | | | |
|---|---|---|---|---|
| EP | 1476217 B1 | 3/2008 | | |
| EP | 1955887 A2 | 8/2008 | | |
| EP | 2462908 A1 | 6/2012 | | |
| FR | 1163907 A | 10/1958 | | |
| GB | 1255395 A | 12/1971 | | |
| WO | WO-8300742 A1 | 3/1983 | | |
| WO | WO-9605873 A1 | 2/1996 | | |
| WO | WO 2001/085248 | 11/2001 | | |
| WO | WO-2004077387 A1 | 9/2004 | | |
| WO | WO-2005025447 A2 | 3/2005 | | |
| WO | WO-2008039223 A1 | 4/2008 | | |
| WO | WO-2009124100 A1 | 10/2009 | | |
| WO | WO-2010142959 A2 | 12/2010 | | |
| WO | WO-2011135285 A1 | 11/2011 | | |
| WO | WO-2011135286 A1 | 11/2011 | | |
| WO | WO-2011135287 A1 | 11/2011 | | |
| WO | WO-2011144888 A1 | 11/2011 | | |
| WO | WO-2012131237 A1 | 10/2012 | | |
| WO | WO-2012143665 A1 | 10/2012 | | |
| WO | WO-2013010907 A1 | 1/2013 | | |
| WO | WO-2013064852 A1 | 5/2013 | | |
| WO | WO-2013083800 A1 | 6/2013 | | |
| WO | WO-2013090810 A1 | 6/2013 | | |
| WO | WO 2013/149078 | 10/2013 | | |
| WO | WO-2014008348 A2 | 1/2014 | | |
| WO | WO-2014016759 A1 | 1/2014 | | |
| WO | WO-2014020440 A1 * | 2/2014 | ....... | A61F 13/00042 |
| WO | WO-2014108476 A1 | 7/2014 | | |
| WO | WO-2014140606 A1 * | 9/2014 | ............ | A61L 15/26 |
| WO | WO-2015022334 A1 | 2/2015 | | |
| WO | WO-2015022340 A1 | 2/2015 | | |
| WO | WO-2016018448 A1 | 2/2016 | | |
| WO | WO-2016174048 A1 | 11/2016 | | |
| WO | WO-2018164803 A1 | 9/2018 | | |
| WO | WO 2018/229008 | 12/2018 | | |

OTHER PUBLICATIONS

International Search Report and Written Opinion, re PCT Application No. PCT/EP2018/065396, dated Jul. 24, 2018.

International Preliminary Report on Patentability for Application No. PCT/EP2018/065396, dated Dec. 26, 2019, 8 pages.

KCI Licensing Inc, "Prevena™ Incision Management System—Clinician Guide—Instructions for Use," 390061 Rev D, Jan. 2010, 10 pages.

KCI Licensing Inc, "Prevena™ Incision Management System—Clinician Guide—Instructions for Use," 390153-WEB Rev B, Jan. 2010, 12 pages.

KCI Licensing, "Prevena™ Incision Management System—Patient Guide", 390064 Rev D, Jan. 2010, 4 pages.

KCI Licensing, "Prevena™ Incision Management System—Patient Guide," 390152-WEB C, Jan. 2011, 6 pages.

KCI Licensing, Prevena™ Incision Management System, Jun. 22, 2010, in 2 pages.

Smith & Nephew, Allevyn Gentle Border Multisite, Jun. 2011, 2 pages.

Smith and Nephew Inc., "Allevyn Wound Dressings Pamphlet," 2008, 2 pages.

Smith and Nephew Medical Ltd., "Reach for the Right Dressing. Reach for Allevyn," Allevyn Educational Booklet, Apr. 2014, 2 pages.

Advantec MFS, Inc., "Membrane Filters" (catalog), retrieved from http://www.advantecmfs.com/catalog/filt/membrane.pdf, on Jan. 29, 2016, Copyright 2001-2011, 17 pages.

Hersle K., et al., "Uses of Dextranomer Absorbent Pads After Cryosurgery of Cutaneous Malignancies," The Journal of Dermatologic Surgery and Oncology, vol. 8, Jan. 1982, pp. 35-37.

Kendall ULTEC Hydrocolloid Dressing (4x4"), Product Ordering Page, web page downloaded on Jul. 13, 2014, 1 page.

Protz K., "Modern Wound Dressings Support the Healing Process," Wound care: Indications and Application, Geriatrie Journal, Apr. 2005, pp. 3333-3339 (17 pages with English translation).

Smith & Nephew, "PICO Single Use Negative Pressure Wound Therapy System," Spiral Booklet, Mar. 2011, 7 pages.

Technology Watch, May 1989, 1 page.

* cited by examiner

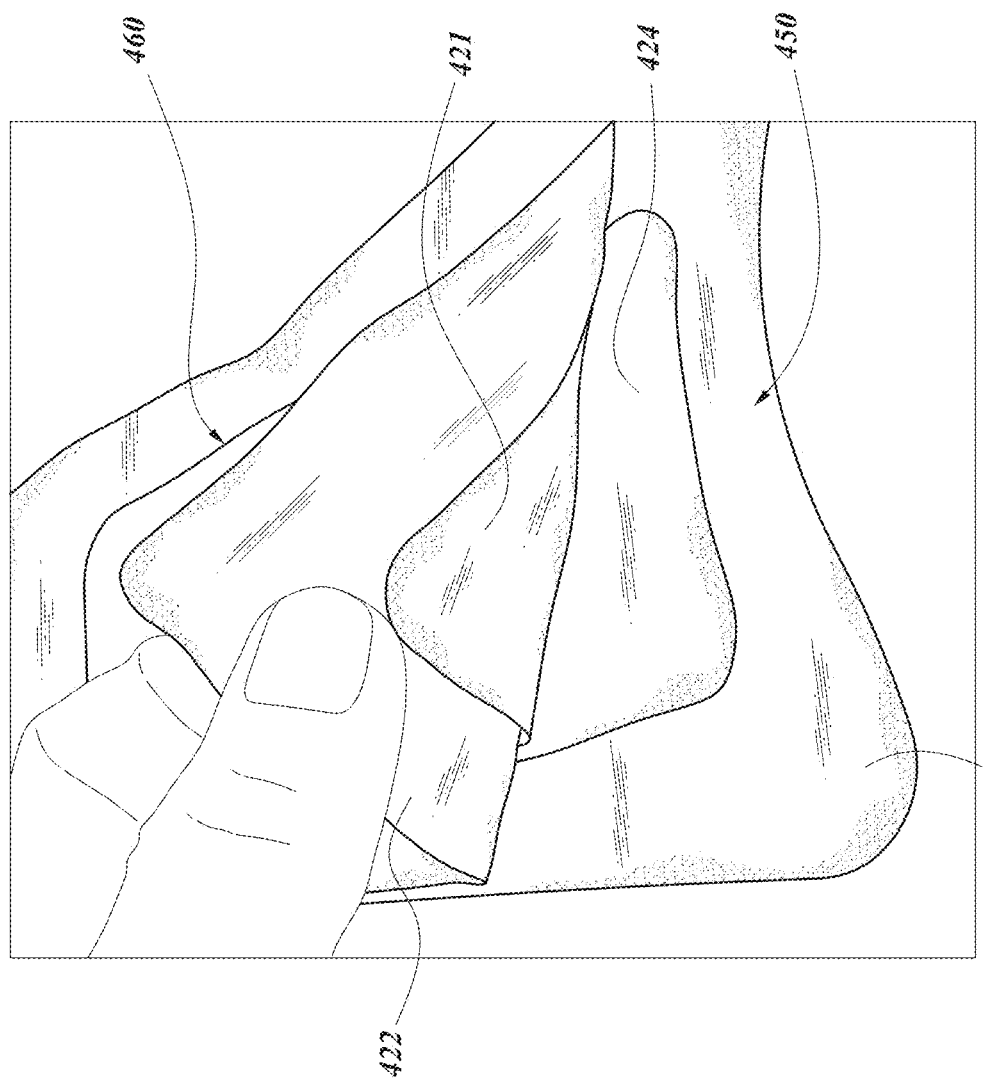
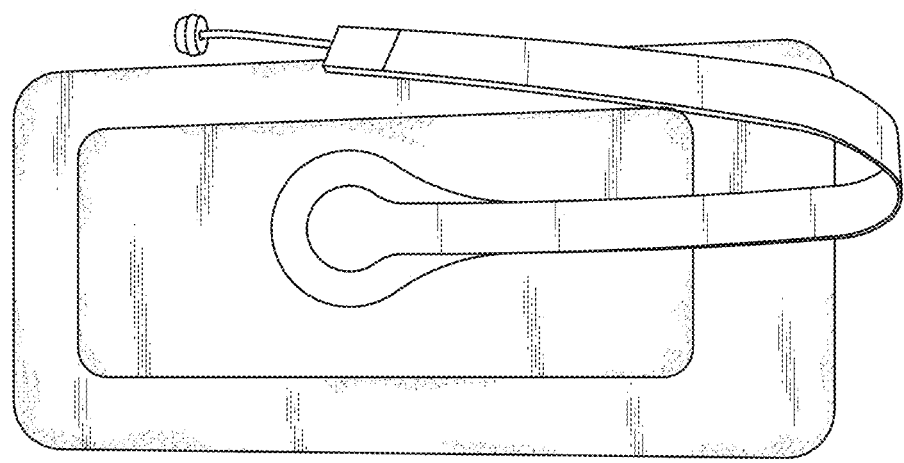

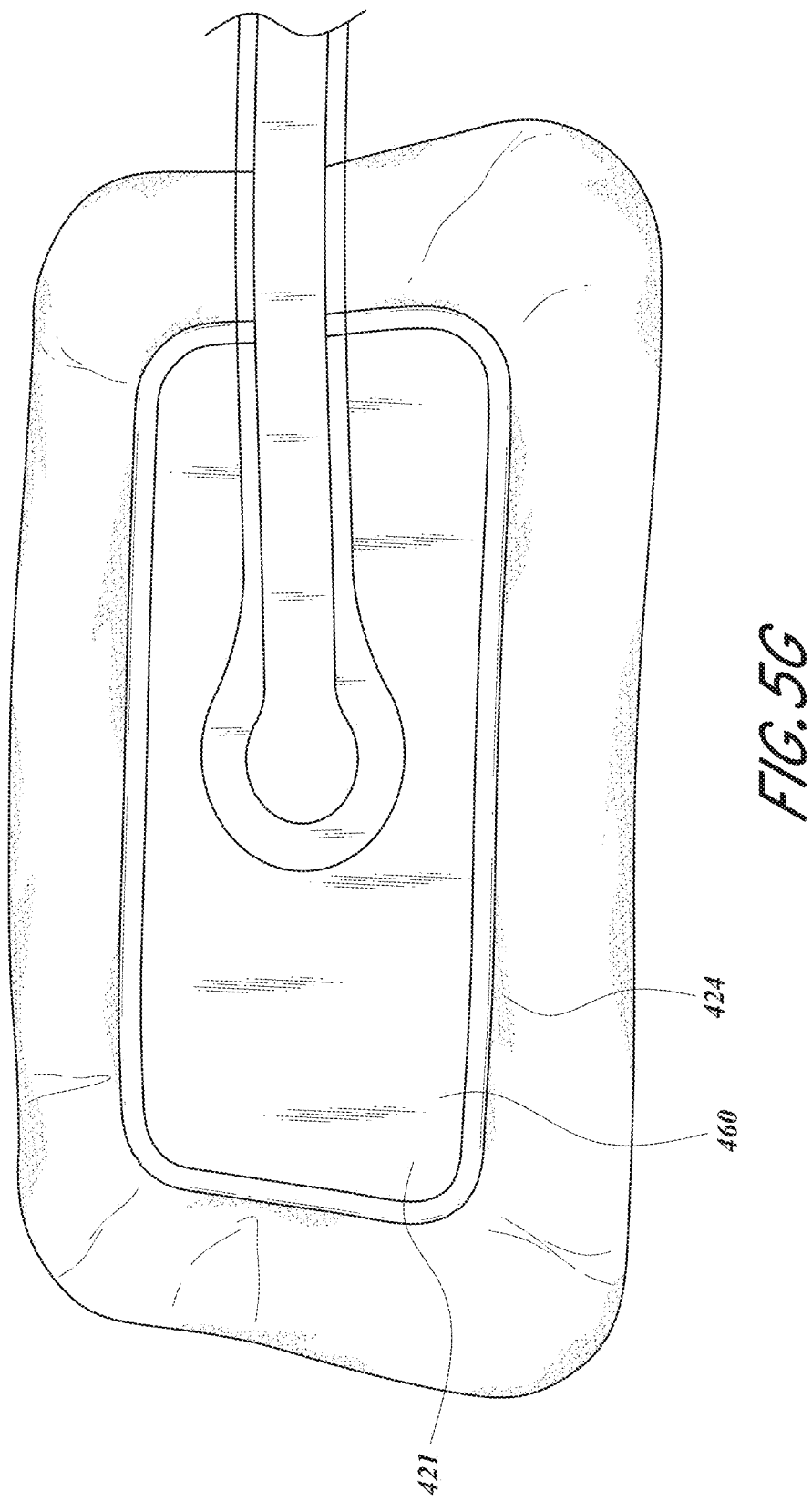

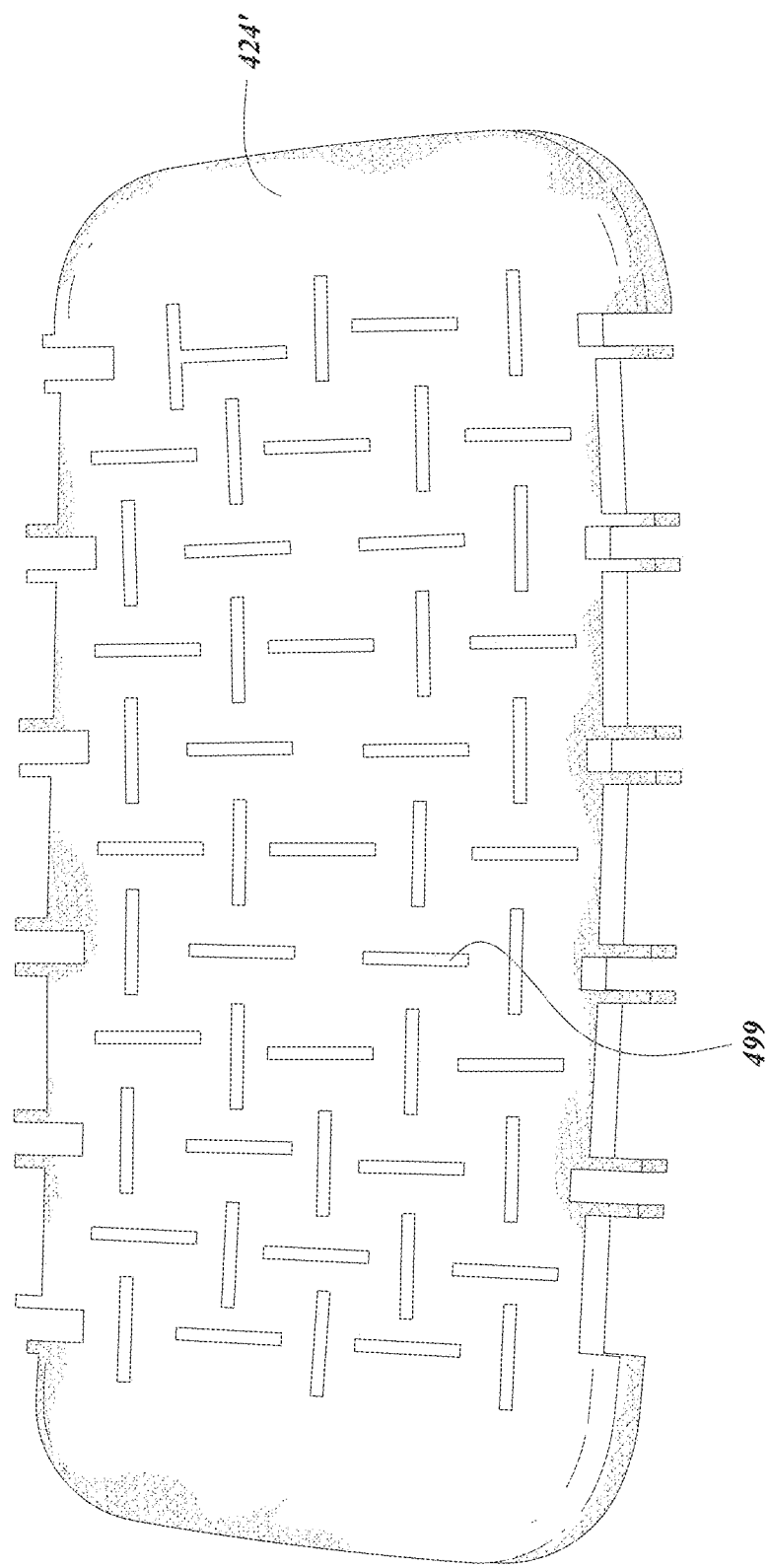

NEGATIVE PRESSURE WOUND THERAPY APPARATUS

CROSS-REFERENCE TO RELATED APPLICATIONS

This application is a U.S. national stage application of International Patent Application No. PCT/EP2018/065396, filed Jun. 11, 2018, which claims priority to U.S. Provisional Application No. 62/519,762, filed on Jun. 14, 2017, which is hereby incorporated by reference in its entirety and made part of this disclosure.

BACKGROUND

Technical Field

Embodiments described herein relate to apparatuses, systems, and methods the treatment of wounds, for example using dressings in combination with negative pressure wound therapy.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

Wound dressings for use in negative pressure can have difficultly conforming to the contours of a patient's body. The inability to conform to the contours of a region of the body can be due to stiff materials, including some absorbent materials, used in the dressing. It may be desirable, in some situations, to provide a conformable lower wound dressing components that include a material layer capable of conforming to a patient.

SUMMARY

Embodiments of the present disclosure relate to apparatuses and methods for wound treatment. Some of the wound treatment apparatuses described herein comprise a negative pressure source or a pump system for providing negative pressure to a wound. Wound treatment apparatuses may also comprise wound dressings that may be used in combination with the negative pressure sources and pump assemblies described herein.

In some aspects, a negative pressure wound therapy apparatus can include a wound dressing. The wound dressing can include a first dressing portion and a second dressing portion overlying the first dressing portion, the first dressing portion can comprise a tissue contact layer configured to be positioned in contact with a wound and/or skin surrounding a wound, wherein the tissue contact layer comprises a first border portion at a perimeter of the tissue contact layer, a first spacer layer, and a first backing layer comprising a first aperture, wherein the first backing layer comprises a second border portion at a perimeter of the first backing layer, wherein the spacer layer is positioned between the tissue contact layer and the first backing layer and the first border portion of the tissue contact layer is sealed to the second border portion of the first backing layer; and the second dressing portion can comprise an intermediate drape comprising a second aperture, wherein the intermediate drape comprises a third border portion at a perimeter of the intermediate drape, an absorbent layer, and a second backing layer comprising a fourth border portion at a perimeter of the second backing layer, wherein the absorbent layer is positioned between the intermediate drape and the second backing layer and the third border portion of the intermediate drape is sealed to the fourth border portion of the second backing layer, and wherein the second dressing portion is attached to the first dressing portion such that the first aperture and the second aperture are fluidly connected, and wherein the second border portion of the first backing layer is unattached to the third border portion of the intermediate drape.

The apparatus of the preceding paragraph may also include any combination of the following features described in this paragraph, among others described herein. In some embodiments, the apparatus can further include a suction port attached to the second backing layer over a third aperture in the second backing layer. In some embodiments, the apparatus can further include a filter configured to prevent or inhibit liquid from entering the suction port. In some embodiments, the apparatus can further include a negative pressure source configured to apply negative pressure through the third aperture in the second backing layer, wherein the first, second, and third apertures are in fluid communication with each other and are configured to provide fluid communication between the negative pressure source and the wound. In some embodiments, the first spacer layer can comprise foam. In some embodiments, the absorbent layer can comprise superabsorbent material. In some embodiments, the apparatus can further include a second spacer layer, wherein the second spacer layer is positioned between the absorbent layer and the intermediate drape. In some embodiments, the second spacer layer can comprise a 3D fabric. In some embodiments, the first backing layer can comprise a flexible material or additional material configured to allow the first backing material to bend. In some embodiments, the first spacer layer can comprise a plurality of slits. In some embodiments, the apparatus can further include a through-hole extending through the absorbent layer. In some embodiments, the through-hole can be aligned underneath a suction port attached to the second backing layer. In some embodiments, the second backing layer can comprise a moisture vapor permeable material. In some embodiments, the tissue contact layer, the first backing layer, the intermediate drape and the second backing layer can all have substantially the same perimeter size and shape. In some embodiments, the first backing layer can be configured to be attached to the intermediate drape at an area around the first aperture and an area around the second aperture. In some embodiments, the first spacer layer can have a smaller perimeter size than the tissue contact layer and the first backing layer. In some embodiments, the first spacer layer can have a rectangular, rounded rectangular, racetrack, oval, circular, triangular, or irregular shape. In some embodiments, the third aperture in the second backing layer can be located at a central region of the second backing layer. In some embodiments, the third aperture in the second backing layer can be located at an edge region of the second backing layer. In some embodiments, the third aperture in the second backing layer can be located at a corner of the second backing layer. In some embodiments, the tissue contact layer can extend across an entire area below the first backing layer. In some embodiments, the tissue contact layer can comprise apertures, pores, or perforations to enable fluid to flow through the tissue contact layer.

In some aspects, a method of treating a wound with a negative pressure wound therapy apparatus, can include positioning a wound dressing over the wound, the wound dressing can include a first portion and a second portion, the first portion comprising a tissue contact layer configured to be positioned in contact with a wound and/or skin surrounding a wound, wherein the tissue contact layer comprises a first border portion at a perimeter of the tissue contact layer, a first spacer layer, and a first backing layer comprising a first aperture, wherein the first backing layer comprises a second border portion at a perimeter of the first backing layer, wherein the spacer layer is positioned between the tissue contact layer and the first backing layer and the first border portion of the tissue contact layer is sealed to the second border portion of the first backing layer, and the second dressing portion comprising an intermediate drape comprising a second aperture, wherein the intermediate drape comprises a third border portion at a perimeter of the intermediate drape, an absorbent layer, and a second backing layer comprising a fourth border portion at a perimeter of the second backing layer, wherein the absorbent layer is positioned between the intermediate drape and the second backing layer and the third border portion of the intermediate drape is sealed to the fourth border portion of the second backing layer, wherein the second dressing portion is attached to the first dressing portion such that the first aperture and the second aperture are fluidly connected, and wherein the second border portion of the first backing layer is unattached to the third border portion of the intermediate drape, and applying negative pressure through a third aperture in the cover layer, wherein the first, second, and third apertures provide fluid communication between a source of negative pressure and the wound.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which:

FIGS. 5A-5G illustrates an embodiment of a negative pressure wound treatment system employing lower wound dressing components including a foam layer capable of conforming to a patient and upper wound dressing components capable of absorbing and storing wound exudate; and FIGS. 6A-6B illustrates embodiments for a foam layer for use in a negative pressure wound treatment system.

DETAILED DESCRIPTION

Figure 1A:
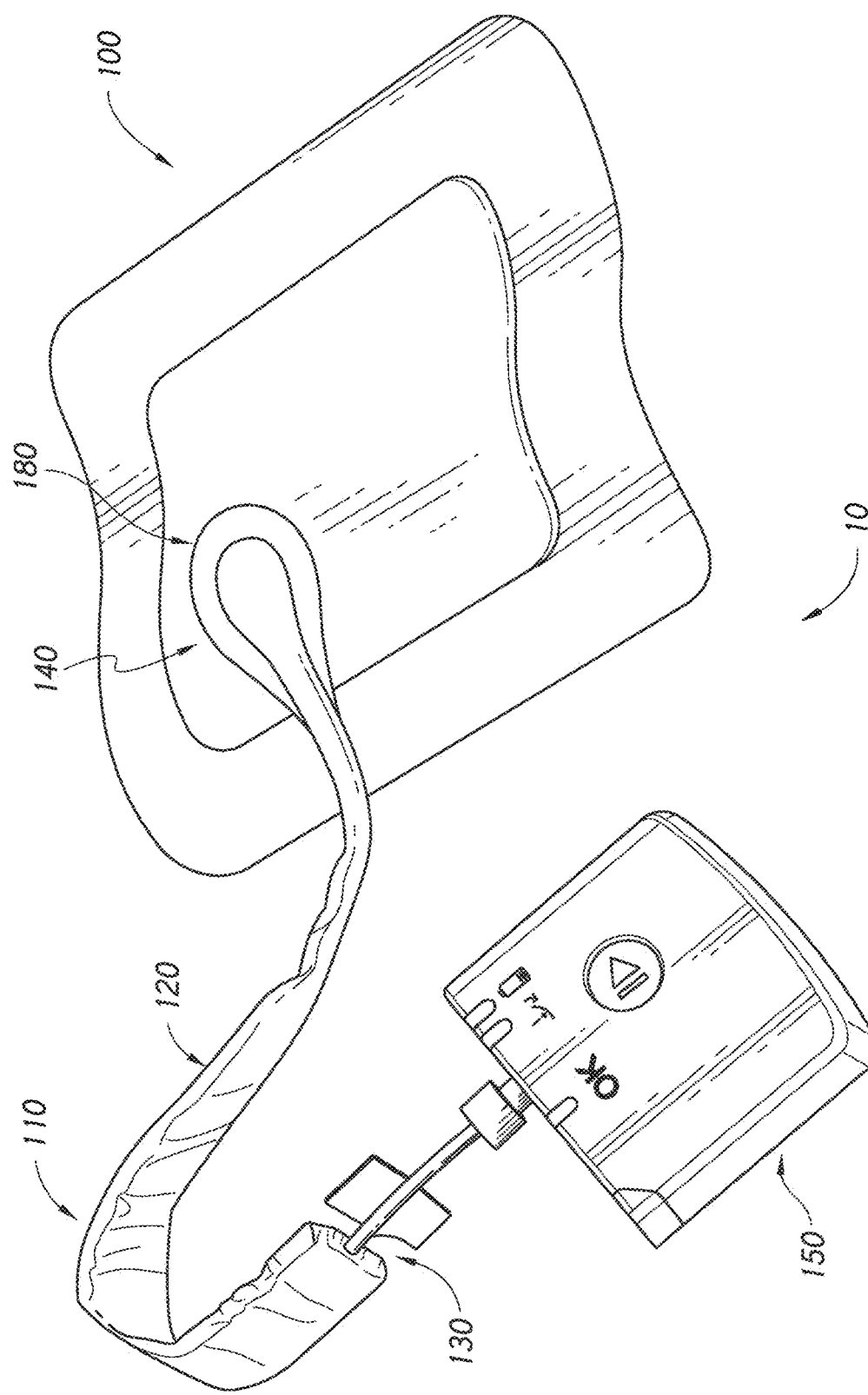
FIG. 1A illustrates an embodiment of a negative pressure wound treatment system employing a flexible fluidic connector and a wound dressing capable of absorbing and storing wound exudate.

Embodiments disclosed herein relate to apparatuses and methods of treating a wound with reduced pressure, including a source of negative pressure and wound dressing components and apparatuses. The apparatuses and components comprising the wound overlay and packing materials, if any, are sometimes collectively referred to herein as dressings.

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as -X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of -X mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (e.g.,-40 mmHg is less than -60 mmHg). Negative pressure that is "more" or "greater" than -X mmHg corresponds to pressure that is further from atmospheric pressure (e.g., -80 mmHg is more than -60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately -80 mmHg, or between about -20 mmHg and -200 mmHg Note that these pressures are relative to normal ambient atmospheric pressure, which can be 760 mmHg. Thus, -200 mmHg would be about 560 mmHg in practical terms. In some embodiments, the pressure range can be between about -40 mmHg and -150 mmHg Alternatively, a pressure range of up to -75 mmHg, up to -80 mmHg or over -80 mmHg can be used. Also in other embodiments a pressure range of below -75 mmHg can be used. Alternatively, a pressure range of over approximately -100 mmHg, or even -150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat).

Embodiments of the wound dressings, wound treatment apparatuses and methods described herein may also be used in combination or in addition to those described in U.S. patent application Ser. No. 12/744,277, filed Sep. 20, 2010, patented as U.S. Pat. No. 8,764,732 on Jul. 1, 2014, titled "WOUND DRESSING," U.S. patent application Ser. No. 12/744,218, filed Sep. 20, 2010, patented as U.S. Pat. No. 8,808,274 on Aug. 19, 2014, titled "WOUND DRESSING," U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158, titled "FLUIDIC CONNECTOR FOR NEGATIVE PRESSURE WOUND THERAPY," the disclosures of which are hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump and/or associated electronics described herein may also be used in combination or in addition to those described in International Application No. PCT/EP2016/059329, filed Apr. 26, 2016, published as WO2016174048 A1 on Nov. 3, 2016, titled "REDUCED PRESSURE APPARATUS AND METHODS."

Figure 1B:
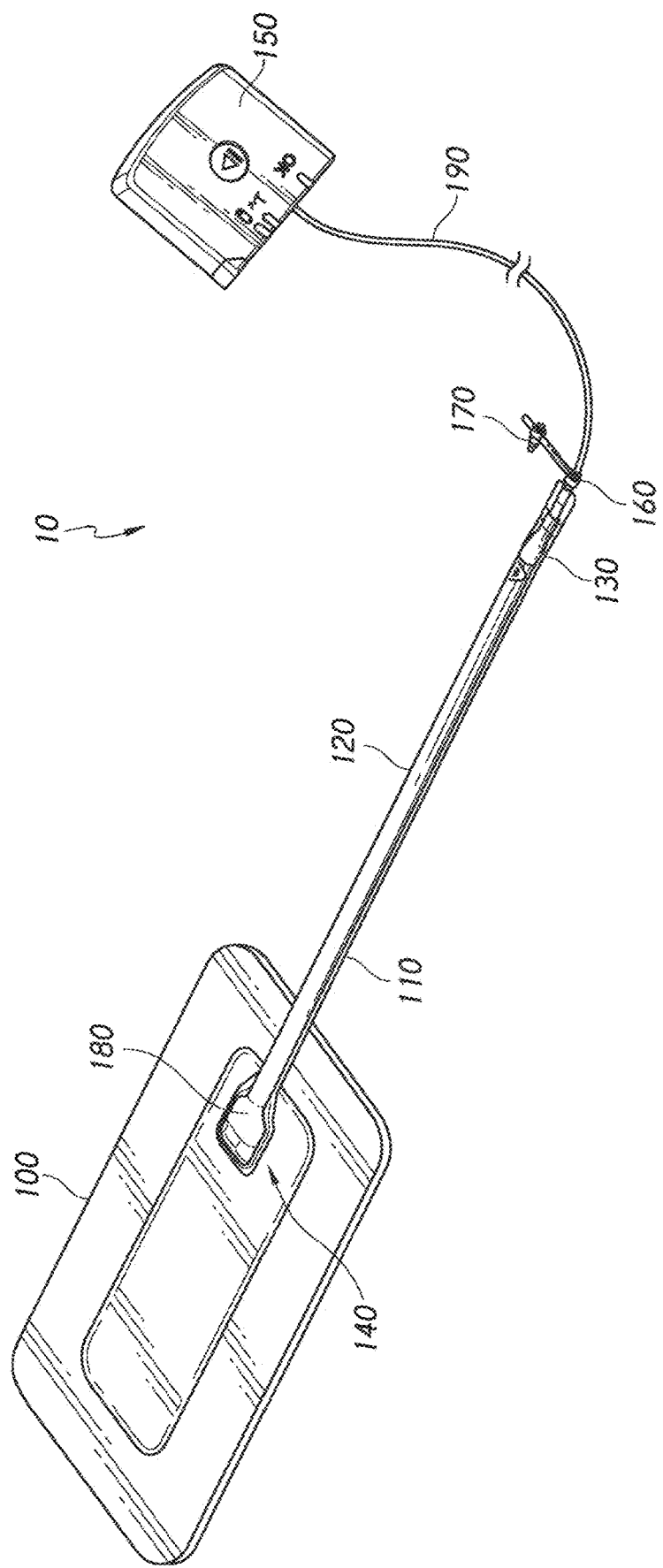
FIG. 1B illustrates an embodiment of a negative pressure wound treatment system employing a flexible fluidic connector and a wound dressing capable of absorbing and storing wound exudate.

FIGS. 1A-B illustrate embodiments of a negative pressure wound treatment system 10 employing a wound dressing 100 in conjunction with a fluidic connector 110. Here, the fluidic connector 110 may comprise an elongate conduit, more preferably a bridge 120 having a proximal end 130 and a distal end 140, and an applicator 180 at the distal end 140 of the bridge 120. An optional coupling 160 is preferably disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 1A-1B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved. In some embodiments, the pump can be miniaturized and portable, although larger conventional pumps may also be used with the dressing 100. In some embodiments, the pump may be attached or mounted onto or adjacent the dressing 100.

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. The wound dressing can include a cover layer for positioning over the layers of the wound dressing. The cover layer can be the upper most layer of the dressing. In some embodiments, the wound dressing can include a second cover layer for positioning over the layers of the wound dressing and any of the integrated components. The second cover layer can be the upper most layer of the dressing or can be a separate envelope that encloses the integrated components of the topical negative pressure system.

Figure 2A:
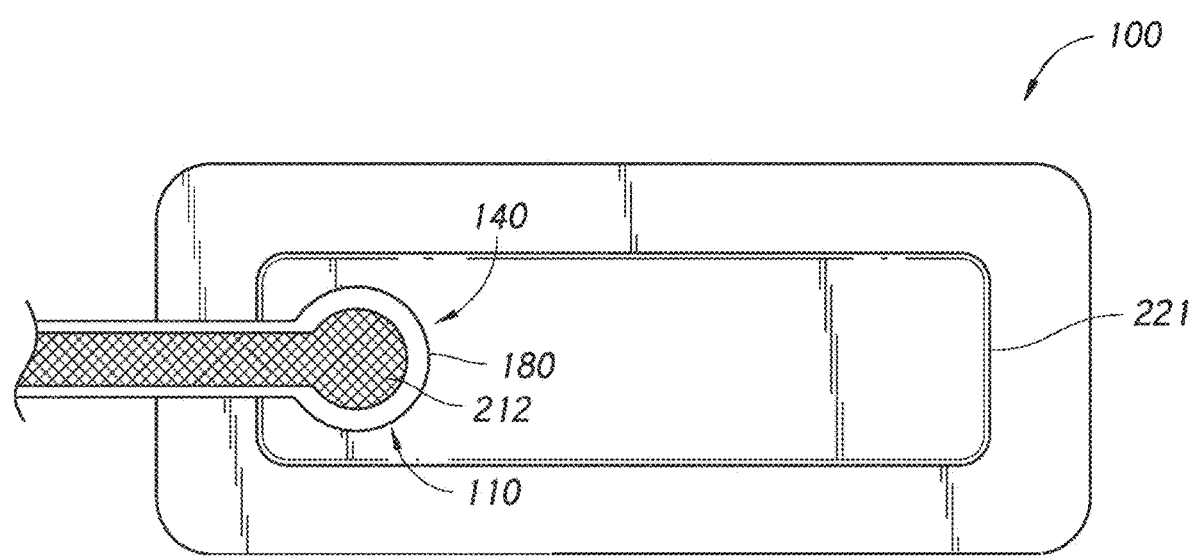
FIG. 2A illustrates an embodiment of a negative pressure wound treatment system employing a flexible fluidic connector and a wound dressing capable of absorbing and storing wound exudate.

As shown in FIG. 2A, the fluidic connector 110 preferably comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 100 may comprise two or more fluidic connectors 110, each comprising one or more heads 140, in fluidic communication therewith. In a preferred embodiment, the head 140 may measure 30 mm along its widest edge. The head 140 forms at least in part the applicator 180, described above, that is configured to seal against a top surface of the wound dressing.

Figure 2B:
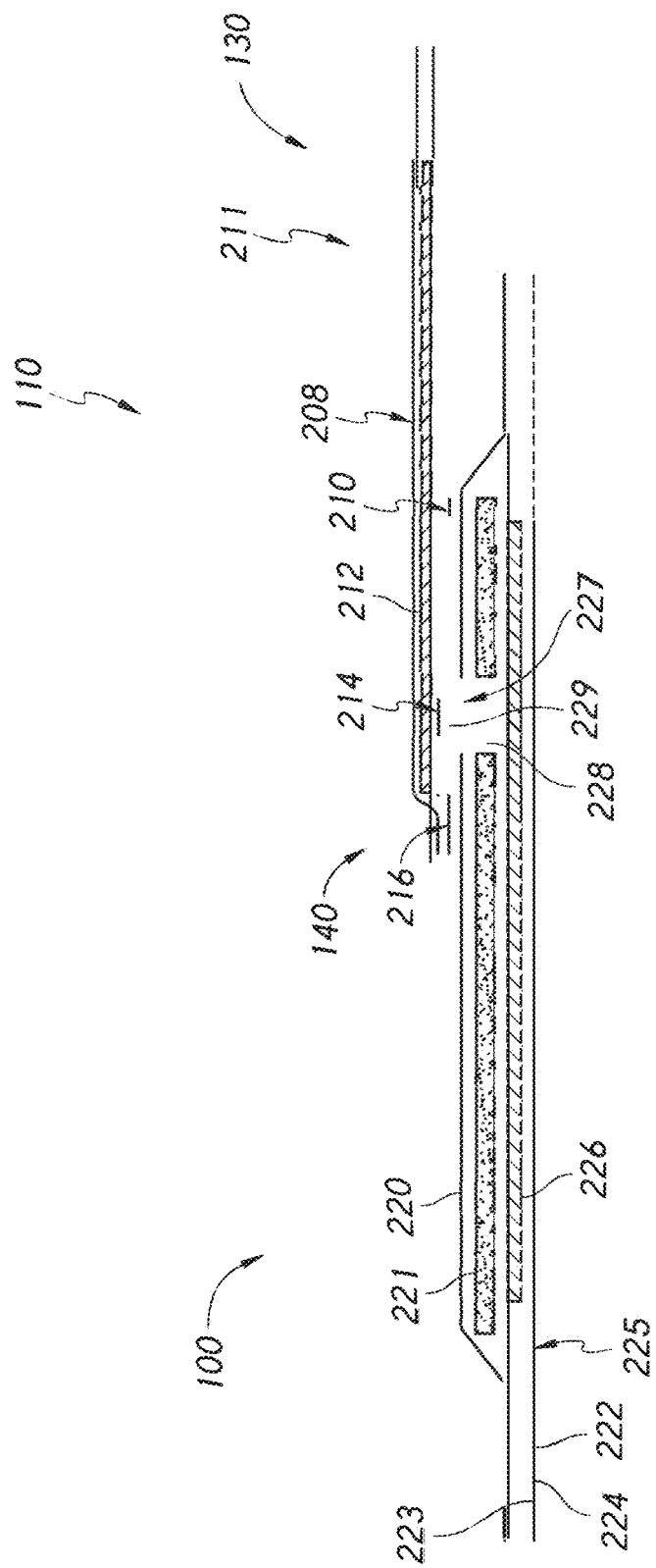
FIG. 2B illustrates a cross section of an embodiment of a fluidic connector connected to a wound dressing.

FIG. 2B illustrates a cross-section through a wound dressing 100 similar to the wound dressing 100 as shown in FIG. 1B and described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," the disclosure of which is hereby incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed as to form a sealed cavity over the wound site. In a preferred embodiment, the dressing 100 comprises a top or cover layer, or backing layer 220 attached to an optional wound contact layer 222, both of which are described in greater detail below. These two layers 220, 222 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 2B, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. The perforations 225 preferably comprise through holes in the wound contact layer 222 which enable fluid to flow through the layer 222. The wound contact layer 222 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound site. In some embodiments, the wound contact layer may comprise perforated polyurethane film The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 preferably ensures that an open air channel can be maintained to communicate negative pressure over the wound area even when the absorbent layer has absorbed substantial amounts of exudates. The layer 226 should preferably remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like mono filament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

Preferably, to improve the liquid flow across the transmission layer 226 (that is to say perpendicular to the channel region formed between the top and bottom spacer layers) the 3D fabric may be treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried out in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material is provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 10 may also aid in drawing fluids towards the backing layer 220.

The material of the absorbent layer 221 may also prevent liquid collected in the wound dressing 100 from flowing freely within the dressing, and preferably acts so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 and/or Chem-Posite™ 11C-450. In some embodiments, the absorbent layer 221 may comprise a composite comprising super-absorbent powder, fibrous material such as cellulose, and bonding fibers. In a preferred embodiment, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 is preferably provided in the backing layer 220 to allow a negative pressure to be applied to the dressing 100. The fluidic connector 110 is preferably attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

Preferably the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 2B a single through hole can be used to produce an opening underlying the fluidic connector 110. It will be appreciated that multiple openings could alternatively be utilized. Additionally should more than one port be utilized according to certain embodiments of the present disclosure one or multiple openings may be made in the absorbent layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 is preferably provided in the absorbent layer 221 beneath the orifice 227 such that the orifice is connected directly to the transmission layer 226 as illustrated in FIG. 2B. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in U.S. patent application Ser. No. 14/418,874, filed Jan. 30, 2015, published as US 2015/0190286 A1 on Jul. 9, 2015, titled "WOUND DRESSING AND METHOD OF TREATMENT," the entirety of which is hereby incorporated by reference, may be provided over the absorbent layer 221 and beneath the backing layer 220.

The backing layer 220 is preferably gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way, an effective chamber is made between the backing layer 220 and a wound site where a negative pressure can be established. The backing layer 220 is preferably sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 preferably comprises two layers; a polyurethane film and an adhesive pattern spread onto the film. The polyurethane film is preferably moisture vapor permeable and may be manufactured from a material that has an increased water transmission rate when wet. In some embodiments, the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which could seep through the seal around the perimeter of the dressing leading to the formation of leaks. As illustrated in FIGS. 2A-2B, the absorbent layer 221 may define a smaller perimeter than that of the backing layer 220, such that a boundary or border region is defined between the edge of the absorbent layer 221 and the edge of the backing layer 220.

As shown in FIG. 2B, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 110, or the orifice 227.

In particular for embodiments with a single fluidic connector 110 and through hole, it may be preferable for the fluidic connector 110 and through hole to be located in an off-center position as illustrated in FIG. 2A. Such a location may permit the dressing 100 to be positioned onto a patient such that the fluidic connector 110 is raised in relation to the remainder of the dressing 100. So positioned, the fluidic connector 110 and the filter 214 (described below) may be less likely to come into contact with wound fluids that could prematurely occlude the filter 214 so as to impair the transmission of negative pressure to the wound site.

Turning now to the fluidic connector 110, preferred embodiments comprise a sealing surface 216, a bridge 211 (corresponding to bridge 120 in FIGS. 1A-1B) with a proximal end 130 and a distal end 140, and a filter 214. The sealing surface 216 preferably forms the applicator previously described that is sealed to the top surface of the wound dressing. In some embodiments a bottom layer of the fluidic connector 110 may comprise the sealing surface 216. The fluidic connector 110 may further comprise an upper surface vertically spaced from the sealing surface 216, which in some embodiments is defined by a separate upper layer of the fluidic connector. In other embodiments, the upper surface and the lower surface may be formed from the same piece of material. In some embodiments, the sealing surface 216 may comprise at least one aperture 229 therein to communicate with the wound dressing. In some embodiments, the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer. In other embodiments, the sealing surface 216 may be positioned over an orifice in the cover layer and an aperture in the absorbent layer 220, permitting the fluidic connector 110 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 is preferably encapsulated by at least one flexible film layer 208, 210 having a proximal and distal end and configured to surround the first fluid passage 212, the distal end of the flexible film being connected to the sealing surface 216. The filter 214 is configured to substantially prevent wound exudate from entering the bridge.

Some embodiments may further comprise an optional second fluid passage positioned above the first fluid passage 212. For example, some embodiments may provide for an air leak may be disposed at the proximal end of the top layer 208 that is configured to provide an air path into the first fluid passage 212 and dressing 100 similar to the suction adapter as described in U.S. Pat. No. 8,801,685, filed Dec. 30, 2011, entitled "APPARATUSES AND METHODS FOR NEGATIVE PRESSURE WOUND THERAPY" the disclosure of which is hereby incorporated by reference in its entirety.

Preferably, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected are preferably suited to channeling wound exudate away from the wound and for transmitting negative pressure and/or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system are preferably conformable and soft, which may help to avoid pressure ulcers and other complications which may result from a wound treatment system being pressed against the skin of a patient.

Preferably, the filter element 214 is impermeable to liquids, but permeable to gases, and is provided to act as a liquid bather and to ensure that no liquids are able to escape from the wound dressing 100. The filter element 214 may also function as a bacterial barrier. Typically the pore size is 0.2 μm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film over the orifice. For example, the filter element 214 may be molded into the fluidic connector 110, or may be adhered to one or both of the top of the cover layer and bottom of the suction adapter 110 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the invention, filter element 214 comprises a support layer and an acrylic co-polymer membrane formed on the support layer. Preferably the wound dressing 100 according to certain embodiments of the present invention uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

Similar to the embodiments of wound dressings described above, some wound dressings comprise a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

In some embodiments, a source of negative pressure (such as a pump) and some or all other components of the topical negative pressure system, such as power source(s), sensor(s), connector(s), user interface component(s) (such as button(s), switch(es), speaker(s), screen(s), etc.) and the like, can be integral with the wound dressing. In some embodiments, the components can be integrated below, within, on top of, and/or adjacent to the backing layer. In some embodiments, the wound dressing can include a second cover layer and/or a second filter layer for positioning over the layers of the wound dressing and any of the integrated components. The second cover layer can be the upper most layer of the dressing or can be a separate envelope that enclosed the integrated components of the topical negative pressure system.

Figure 3A:
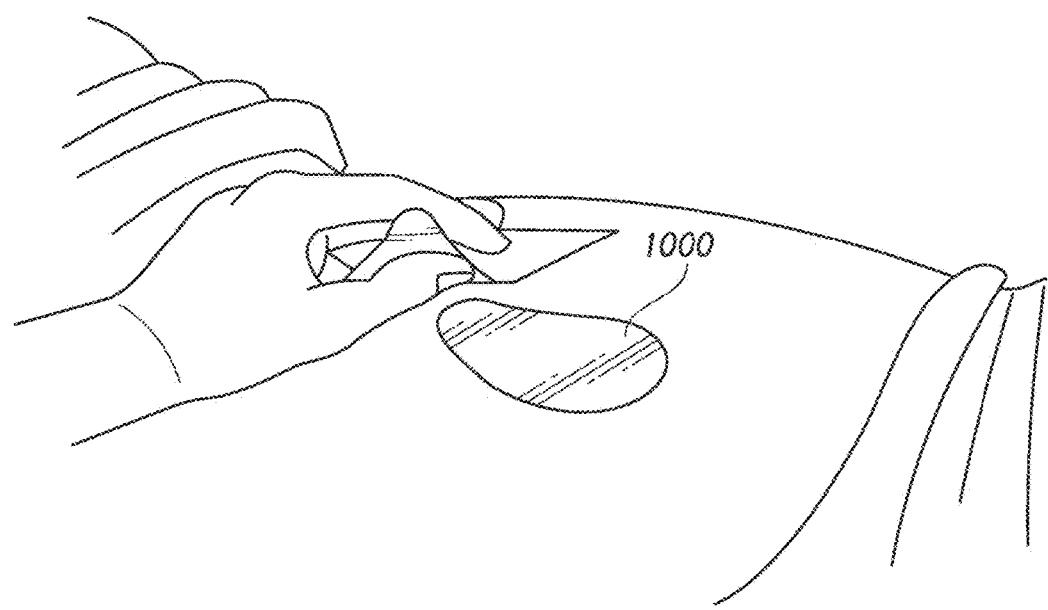
FIGS. 3A-D illustrate the use and application of an embodiment of a wound treatment system onto a patient.

FIGS. 3A-D illustrate the use of an embodiment of a negative pressure therapy wound treatment system being used to treat a wound site on a patient. FIG. 3A shows a wound site 1000 being cleaned and prepared for treatment. Here, the healthy skin surrounding the wound site 1000 is preferably cleaned and excess hair removed or shaved. The wound site 1000 may also be irrigated with sterile saline solution if necessary. Optionally, a skin protectant may be applied to the skin surrounding the wound site 1000. If necessary, a wound packing material, such as foam or gauze, may be placed in the wound site 1000. This may be preferable if the wound site 1000 is a deeper wound.

Figure 3B:
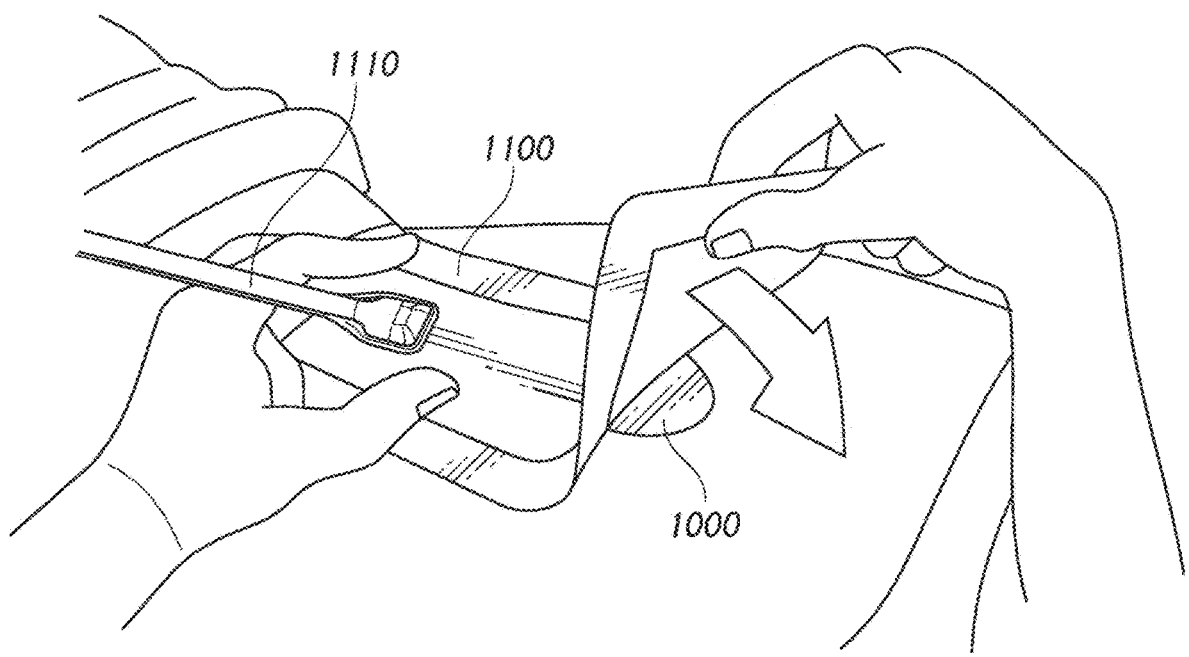

After the skin surrounding the wound site 1000 is dry, and with reference now to FIG. 3B, the wound dressing 1100 may be positioned and placed over the wound site 1000. Preferably, the wound dressing 1100 is placed with the wound contact layer over and/or in contact with the wound site 1000. In some embodiments, an adhesive layer is provided on the lower surface of the wound contact layer, which may in some cases be protected by an optional release layer to be removed prior to placement of the wound dressing 1100 over the wound site 1000. Preferably, the dressing 1100 is positioned such that the fluidic connector 1110 is in a raised position with respect to the remainder of the dressing 1100 so as to avoid fluid pooling around the port. In some embodiments, the dressing 1100 is positioned so that the fluidic connector 1110 is not directly overlying the wound, and is level with or at a higher point than the wound. To help ensure adequate sealing for TNP, the edges of the dressing 1100 are preferably smoothed over to avoid creases or folds.

Figure 3C:
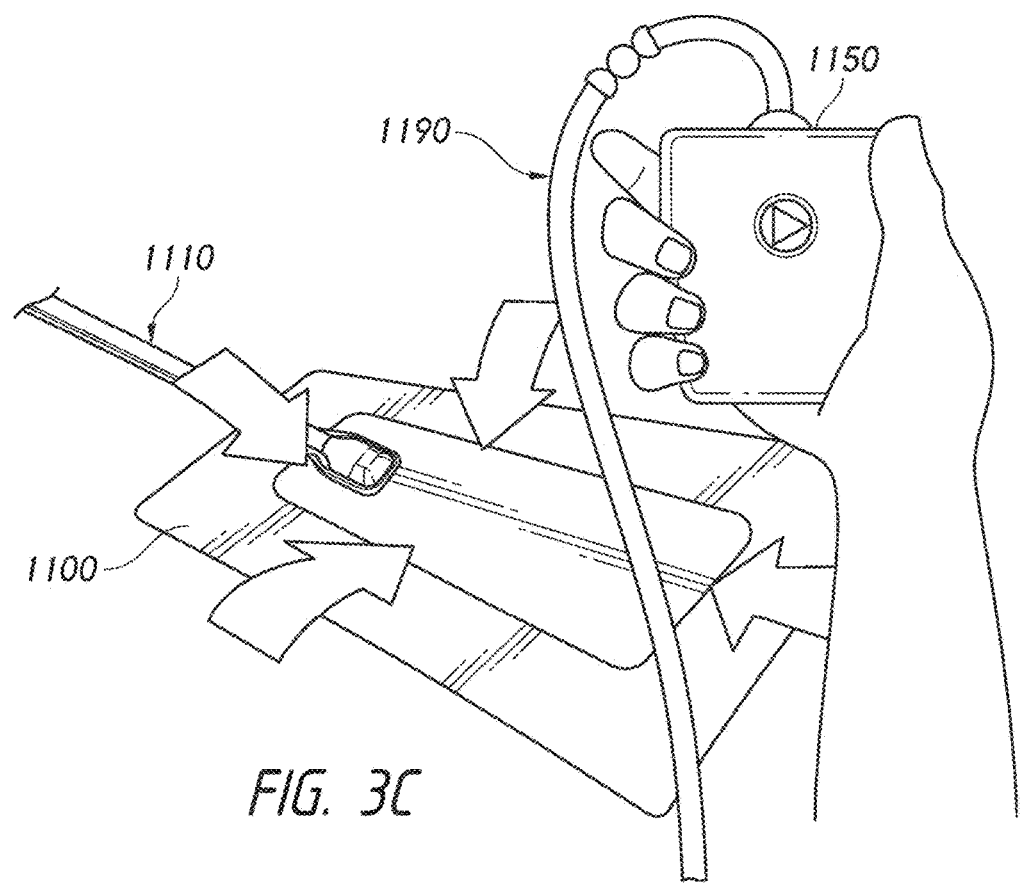

With reference now to FIG. 3C, the dressing 1100 is connected to the pump 1150. The pump 1150 is configured to apply negative pressure to the wound site via the dressing 1100, and typically through a conduit. In some embodiments, and as described herein, a fluidic connector 1110 may be used to join the conduit 1190 from the pump 1150 to the dressing 1100. Where the fluidic connector is adhered to the top layer of the wound dressing, a length of tubing may be coupled at a first end of the fluidic connector such that the tubing, or conduit, extends away from the fluidic connector parallel to the top of the dressing. In some embodiments, the conduit may comprise a fluidic connector. It is expressly contemplated that a conduit may be a soft bridge, a hard tube, or any other apparatus which may serve to transport fluid. Upon the application of negative pressure with the pump 1150, the dressing 1100 may in some embodiments partially collapse and present a wrinkled appearance as a result of the evacuation of some or all of the air underneath the dressing 1100. In some embodiments, the pump 1150 may be configured to detect if any leaks are present in the dressing 1100, such as at the interface between the dressing 1100 and the skin surrounding the wound site 1000. Should a leak be found, such leak is preferably remedied prior to continuing treatment.

Figure 3D:
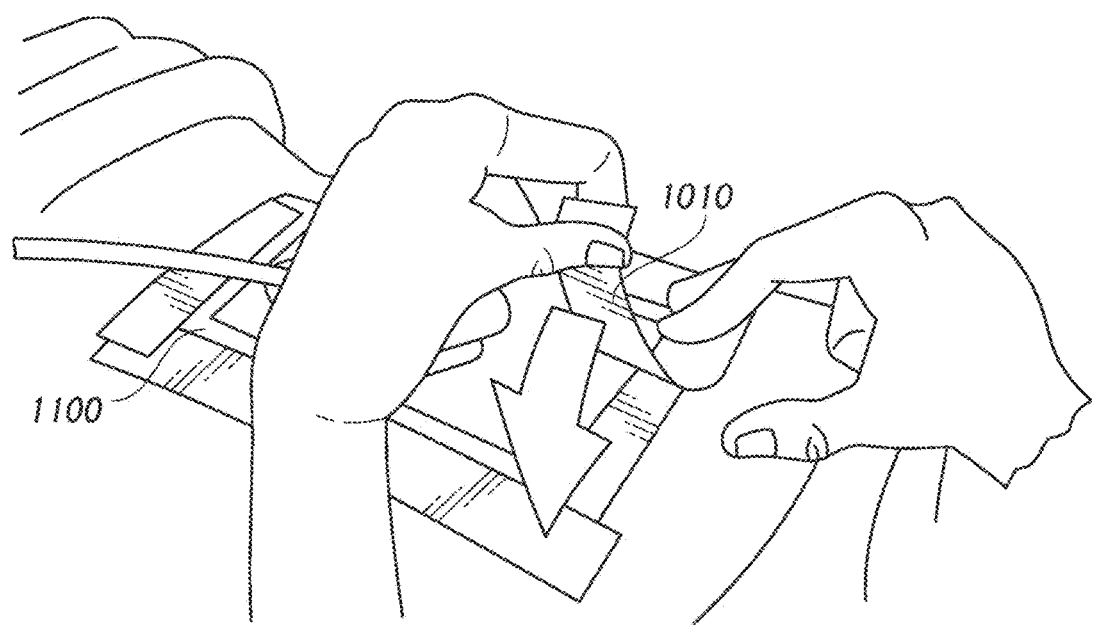

Turning to FIG. 3D, additional fixation strips 1010 may also be attached around the edges of the dressing 1100. Such fixation strips 1010 may be advantageous in some situations so as to provide additional sealing against the skin of the patient surrounding the wound site 1000. For example, the fixation strips 1010 may provide additional sealing for when a patient is more mobile. In some cases, the fixation strips 1010 may be used prior to activation of the pump 1150, particularly if the dressing 1100 is placed over a difficult to reach or contoured area.

Treatment of the wound site 1000 preferably continues until the wound has reached a desired level of healing. In some embodiments, it may be desirable to replace the dressing 1100 after a certain time period has elapsed, or if the dressing is full of wound fluids. During such changes, the pump 1150 may be kept, with just the dressing 1100 being changed.

Figure 4A:
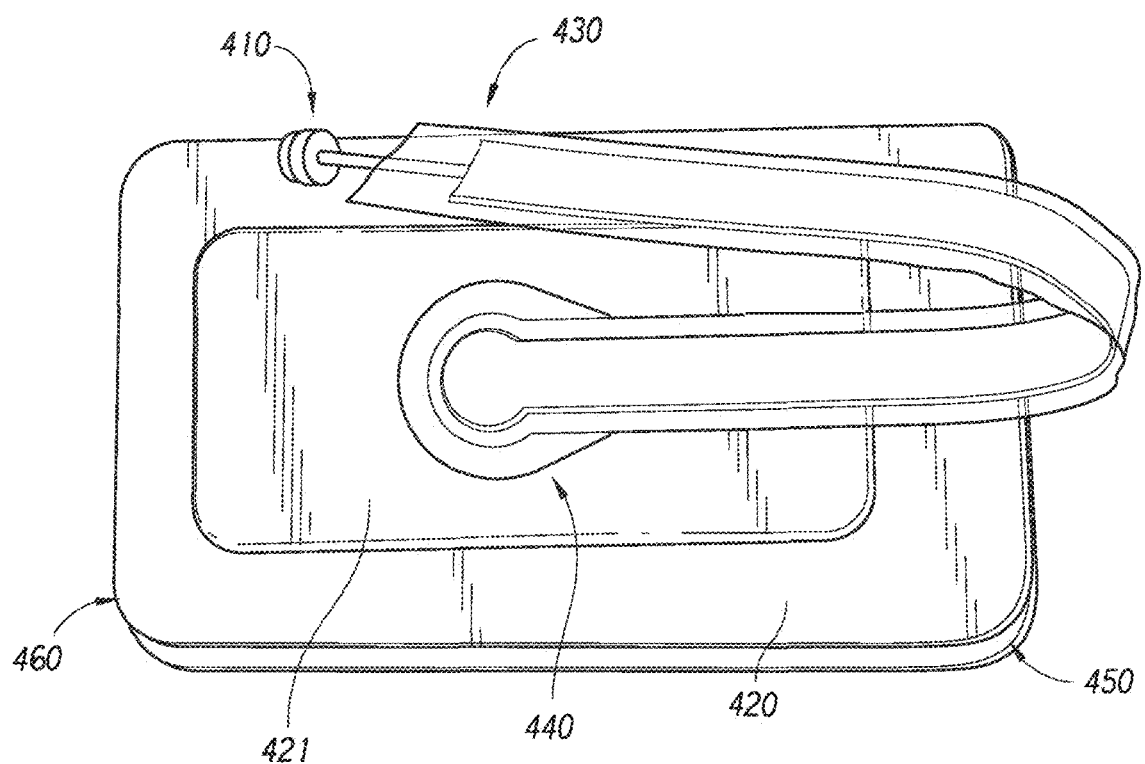
FIG. 4A illustrates a top view of an embodiment of a negative pressure wound treatment system employing lower wound dressing components including a foam layer capable of conforming to a patient and upper wound dressing components capable of absorbing and storing wound exudate.

FIG. 4A illustrates a top view of an embodiment of a negative pressure wound treatment system employing lower wound dressing components 450 including a conforming manifold system and upper wound dressing components 460 capable of absorbing and storing wound exudate. The negative pressure wound dressing as illustrated in FIG. 4A includes a wound dressing similar to the wound dressing described with reference to FIGS. 1A-1B and 2A-2B but the wound dressing includes additional layers that form the lower wound dressing components 450 including a conforming manifold system. In some embodiments, the lower wound dressing components 450 can be positioned below the wound dressing components described with reference to FIGS. 1A-1B and 2A-2B. The wound dressing illustrated in FIG. 4A includes upper wound dressing components 460 including a wound cover layer or top backing layer 420 and an absorbent layer 421 similar to the components described with reference to FIGS. 1A-1B and 2A-2B. The upper wound dressing components can also include an intermediate drape (not shown) below the absorbent layer. A border or perimeter portion of the intermediate drape can be sealed to the top backing layer at a perimeter of the top backing layer. The intermediate drape can include an aperture to provide fluid communication with a conforming system 450 positioned between the intermediate drape and the wound as described herein.

Figure 4B:
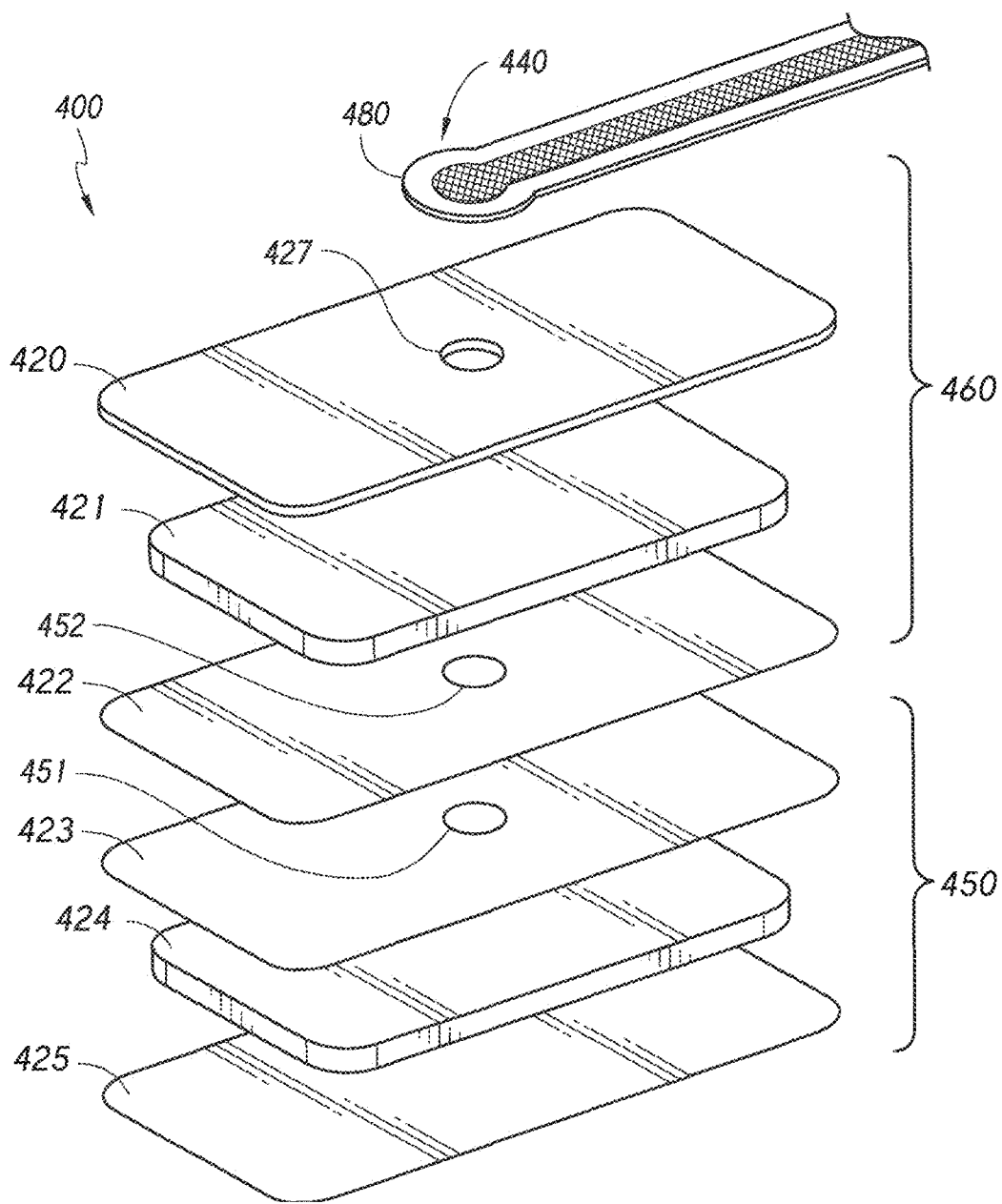
FIG. 4B illustrates an embodiment of a negative pressure wound treatment system employing lower wound dressing components including a foam layer capable of conforming to a patient and upper wound dressing components capable of absorbing and storing wound exudate.
Figure 4C:
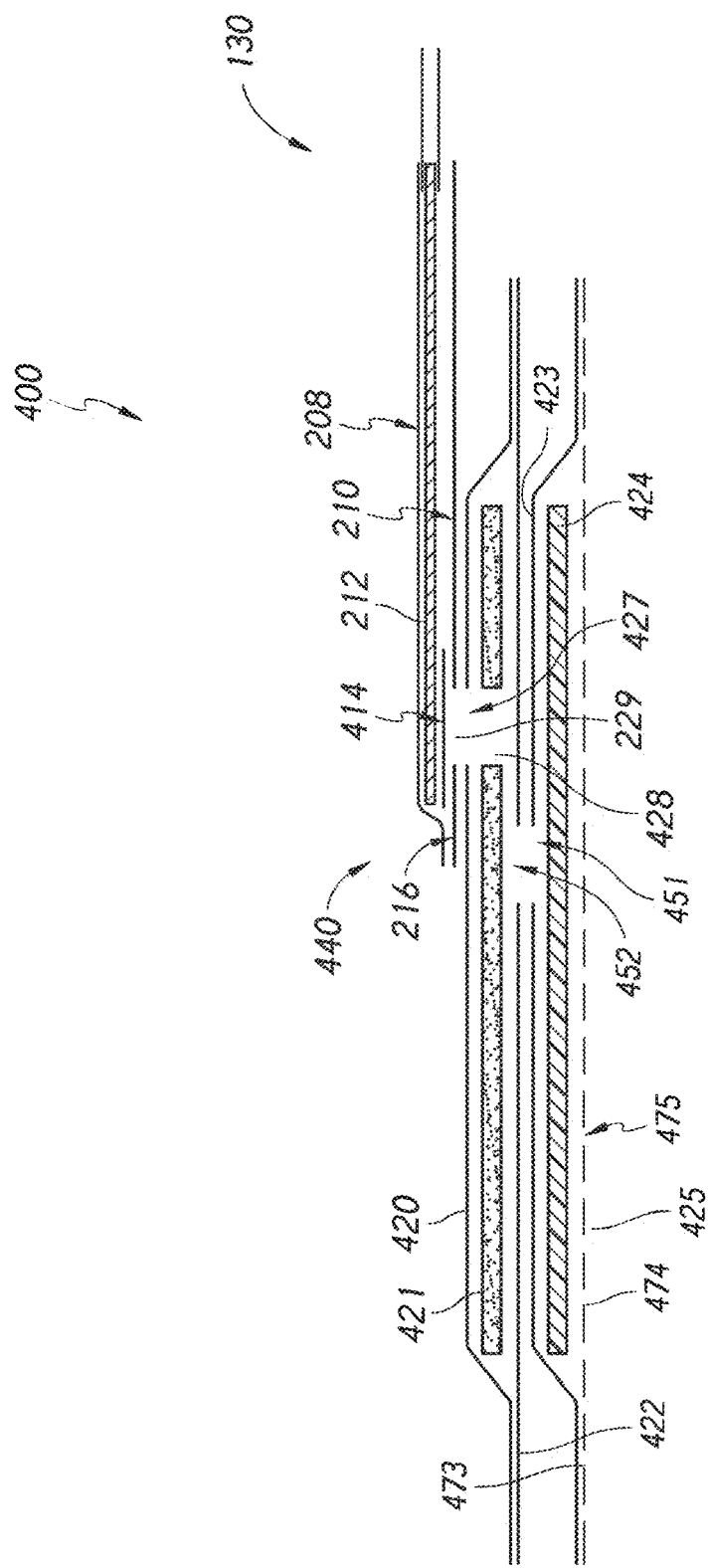
FIG. 4C illustrates a cross-section of an embodiment of a negative pressure wound treatment system employing lower wound dressing components including a foam layer capable of conforming to a patient and upper wound dressing components capable of absorbing and storing wound exudate.

FIG. 4B-4C illustrate the layers of an embodiment of a negative pressure wound treatment system of FIG. 4A employing lower wound dressing components 450 including a conforming manifold system and upper wound dressing components 460 capable of absorbing and storing wound exudate.

As illustrated in FIG. 4B-4C, the wound dressing 400 can include upper wound dressing components 460 including an absorbent material and lower wound dressing components 450 including a conforming manifold. The lower wound dressing components 450 can include a lower wound contact layer 425, a conforming manifold or foam layer 424, and a first backing layer 423. The lower wound contact layer 425 can be similar to wound contact layer 222 described with reference to FIG. 2B and can be placed in contact with the wound. As used herein, the wound contact layer and tissue contact layer can be used interchangibly. The conforming manifold can include a foam layer 424. In some embodiments, the foam layer comprises a rectangular, rounded rectangular, racetrack, oval, circular, triangular, or irregular shape with different angles and different side sizes. The foam layer can have a smaller perimeter size than the tissue contact layer. The foam layer 424 can include a reticulated foam and/or other foam, filler, transmission, or spacer layer known in the art. In some embodiments, the conforming manifold can comprise a 30 ppi reticulated foam. In some embodiments, the conforming manifold can comprise a 6 mm 30 ppi reticulated foam. As described herein, the conforming manifold can include a foam material and/or other spacer or transmission layer. As used herein, the terms foam, spacer, and/or transmission layer can be used interchangeably to refer to the layer of material in the dressing configured to distribute negative pressure throughout the wound area. The first backing layer 423 can be a moisture vapor permeable film similar to the cover layer or backing layer described with reference to FIG. 2B. In other embodiments, the first backing layer 423 can be a non-permeable film In some embodiments, the first backing layer 423 can be another material that is impermeable to both liquid and gas. In some embodiments, the wound contact layer 425 extends across an entire area below the first backing layer 423. In some embodiments, the wound contact layer and the first backing layer can have substantially the same perimeter size and shape. The foam layer can have a smaller perimeter size than the wound contact layer and the first backing layer. The perimeter of the first backing layer 423 can be sealed to the outer perimeter of the lower wound contact layer 425 enclosing and covering the foam layer 424. The first backing layer 423 can include an aperture or opening 451 in the first backing layer 423. The aperture or opening 451 can be positioned in a center portion of the first backing layer 423 as shown in FIG. 4B.

The lower wound dressing components 450 can be used in combination with upper wound dressing components 460 including an absorbent material similar to those described with reference to FIG. 2B. The wound dressing system can include an intermediate drape 422 provided above the first backing layer. The intermediate drape 422 can include an aperture or opening 452. In some embodiments, the aperture or opening 452 can be positioned in a center portion of the intermediate drape 422. The aperture 452 can align with and sealed to aperture 451 of the first backing layer 423. In some embodiments, an area around the first aperture can be sealed to an area around the second aperture to attach the first backing layer to the intermediate drape. The apertures 451 and 452 can provide fluid communication between the two layers.

As shown in FIG. 4B and 4C, an absorbent layer 421 can be provided above the intermediate drape 422. The absorbent layer 421 can be similar to the absorbent material 221 described with reference to FIG. 2B. A second backing layer 420 can be provided above the absorbent layer 421. The second backing layer 420 can be similar to the backing layer or cover layer 220 described with reference to FIG. 2B. In some embodiments, the second backing layer 420 can be the same material as the first backing layer 423. In other embodiments, the second backing layer 420 can be a different material than the first backing layer 423. In some embodiments, the tissue contact layer, the first backing layer, the intermediate drape and the second backing layer all have substantially the same perimeter size and shape as shown in FIGS. 4A-4C. In some embodiments, a spacer layer or transmission layer (not shown) can be provided as part of the upper would dressing components 460. In some embodiments, the spacer layer can be positioned between the intermediate drape 422 and the absorbent layer 421 similar to the layered construction described with reference to FIG. 2B. In some embodiments, the absorbent material 421 can be used without the spacer layer material. In some embodiments, the upper wound dressing components 460 can include multiple absorbent and/or multiple spacer layers.

The second backing layer 420 can include an aperture or opening 427. A fluidic connector 440 can be provided above the aperture or opening 427 in the second backing layer 420. The fluidic connector 440 can be similar to the fluidic connector 110 described with reference to FIG. 2A-2B. The fluidic connector 440 may comprise an elongate conduit and an applicator 480. As shown in FIG. 4C, the applicator 480 can be positioned above and sealed to or around the aperture or opening 427 in the second backing layer 420 for delivering negative pressure to the wound dressing 400.

FIG. 4C illustrates a cross-section of an embodiment of a negative pressure wound treatment system employing lower wound dressing components including a foam layer capable of conforming to a patient and upper wound dressing components capable of absorbing and storing wound exudate. Unless otherwise noted, reference numerals and like-named components in FIG. 4C refer to components that are the same as or generally similar to the components of FIG. 2B. In some embodiments, a port 440 can be provided over an opening 427 in the second backing layer 420. The port can include a filter 414. In some embodiments, a negative pressure source can be in fluid communication with the port 440 and/or opening 427 in the second backing layer. The negative pressure source can apply negative pressure through the opening or aperture 427 in the second backing layer. The apertures 427, 452, 451 in the second backing layer 420, intermediate layer 422, and first backing layer 423 can provide fluid communication between the negative pressure source and the wound. In some embodiments, the absorbent layer 421 can include a through-hole 428 extending through the absorbent layer 421. In some embodiments, the through-hole 428 can be aligned underneath the filter 414 as illustrated in FIG. 4C. In other embodiments, the through-hole 428 can be offset from the filter 414. In some embodiments, the components of the wound dressing can be kept aligned by using a central dab of glue.

In some embodiments, aperture 451 and aperture 452 can be positioned at a central portion of the intermediate drape 422 and first backing layer 423, respectively, as shown in FIGS. 4A-4C. In some embodiments, aperture 451 and aperture 452 can be positioned in a corner, at an edge, or in any portion of the intermediate drape 422 and first backing layer 423, respectively. In some embodiments, the apertures or openings 451, 452 can be a rectangular opening or slit forming a channel when aligned and sealed to the aperture or opening 452. In some embodiments, the intermediate drape 422 and first backing layer 423 can have two or more apertures or openings to provide fluid communication between the conforming manifold system 450 and the absorbent material of the wound dressing. In some embodiments, the apertures 451 and 452 can be positioned offset from the filter 414 and through-hole 428 as illustrated in FIG. 4C. In other embodiments, the apertures 451 and 452 can be aligned underneath the filter 414 and through-hole 428.

The wound dressing system includes the lower wound dressing components with the conforming manifold for conforming to a patient in communication with absorbent materials of the upper wound dressing components for absorbing and storing wound exudate. In some embodiments, the absorbent dressing components as described above can be stiffer or more rigid than foam or transmission layers that may be utilized as components of the dressing. Therefore, in some embodiments, the stiffer) components of the dressing can be decoupled from a foam or a lower spacer layer as described herein.

The structure described herein can allow the dressing to have the ability to conform to a contoured region of the body of a patient while also allowing for the stiffer absorbent dressing components to be incorporated into the upper wound dressing components 460 of the wound dressing. In some embodiments, when using a conforming manifold system, the upper wound dressing components can fold like an anemone when negative pressure is applied as described further herein. In some embodiments, the foam can have compressibility to generate good moulding and absence of imprinting. Additionally, in some embodiments, the lower wound dressing components can provide a more complete and effective seal to the patient's body.

Figure 5C:
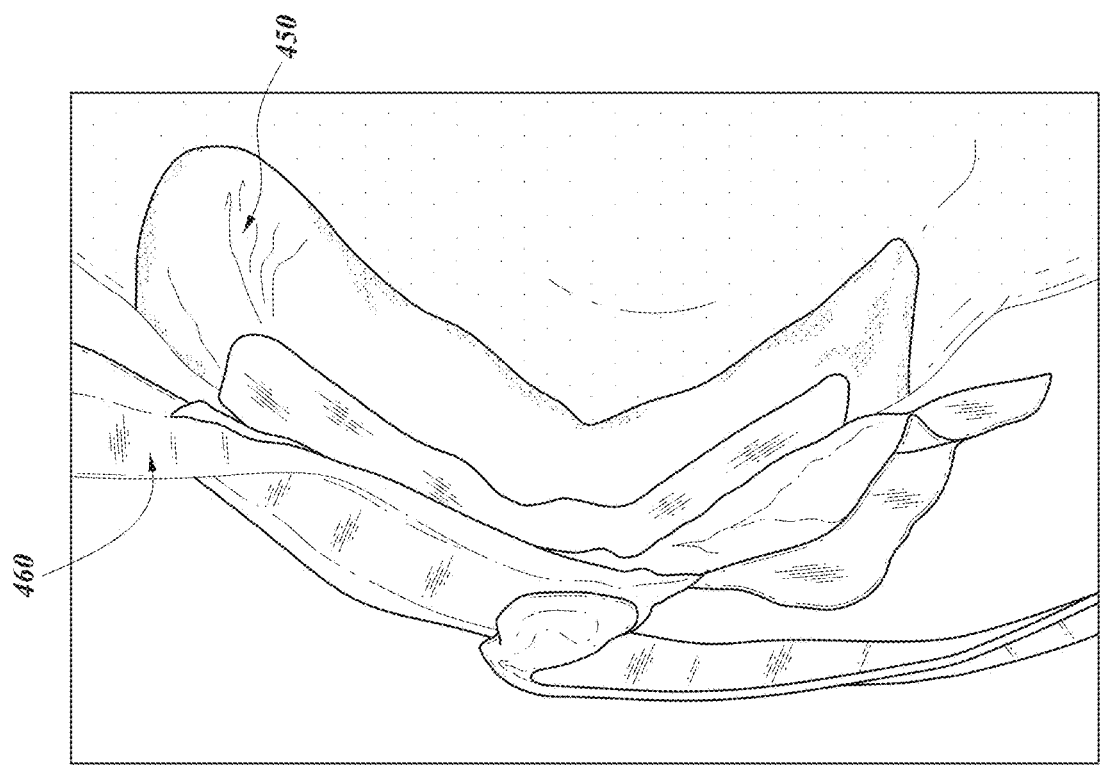

FIGS. 5A-5G illustrates an embodiment of a negative pressure wound treatment system employing lower wound dressing components including a foam layer capable of conforming to a patient and upper wound dressing components capable of absorbing and storing wound exudate. FIG. 5A illustrates a top view of the wound dressing described herein. FIG. 5B illustrates an embodiment of the wound dressing with the upper wound dressing components 460 lifted away from the lower wound dressing components 450. As illustrated in FIG. 5B, the lower wound dressing components include the foam or lower spacer layer 424 enclosed within the first backing layer 423 and the lower wound contact layer (not shown). The absorbent material 421 is illustrated enclosed within the intermediate drape 422 and the second backing layer 420 forming the upper wound dressing components 460 above the lower wound dressing components 450.

FIG. 5C illustrate an embodiment of the wound dressing with lower wound dressing components positioned on a contoured portion of a patient's body. As illustrated in FIG. 5C, the lower wound dressing components 450 are placed on the contoured body portion of a patient and sealed to the skin. In some embodiments, the lower wound dressing components 450 will wrap around and conform to the body while the upper wound dressing components 460 bend and conform less to the area of the body. In some embodiments, the first backing layer 423 and/or the wound contact layer 425 can be flexible enough to not restrict movement or bending of the lower spacer layer 424 as it conforms to the contoured shape. In some embodiments, the first backing layer 423 and/or the wound contact layer 425 can have additional material so as not to restrict movement of bending of the lower spacer layer 424 as it conforms to the contoured shape.

Figure 5D:
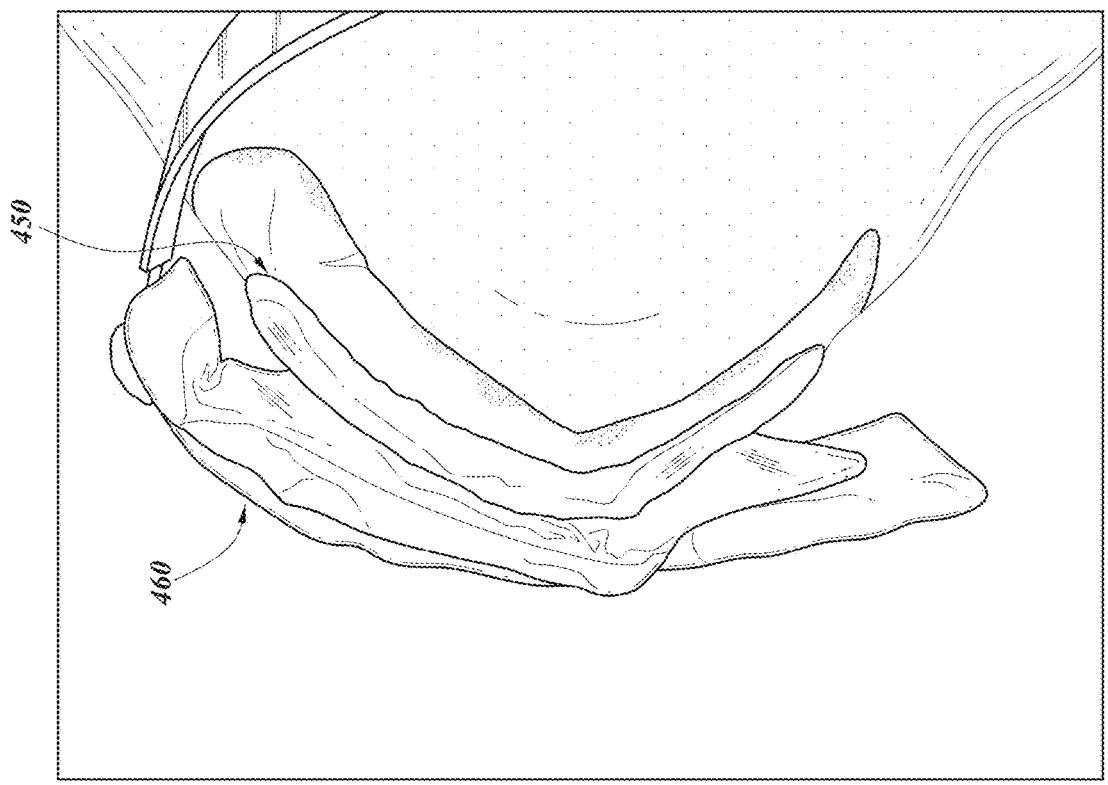
Figure 5F:
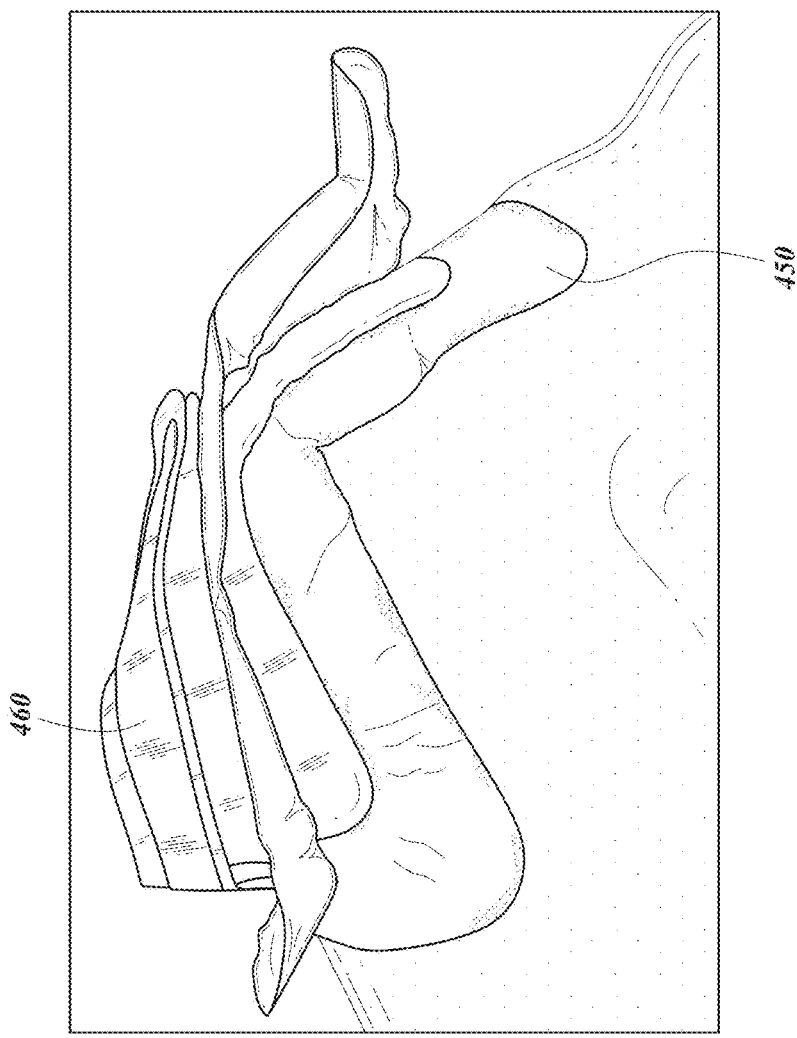
Figure 5E:
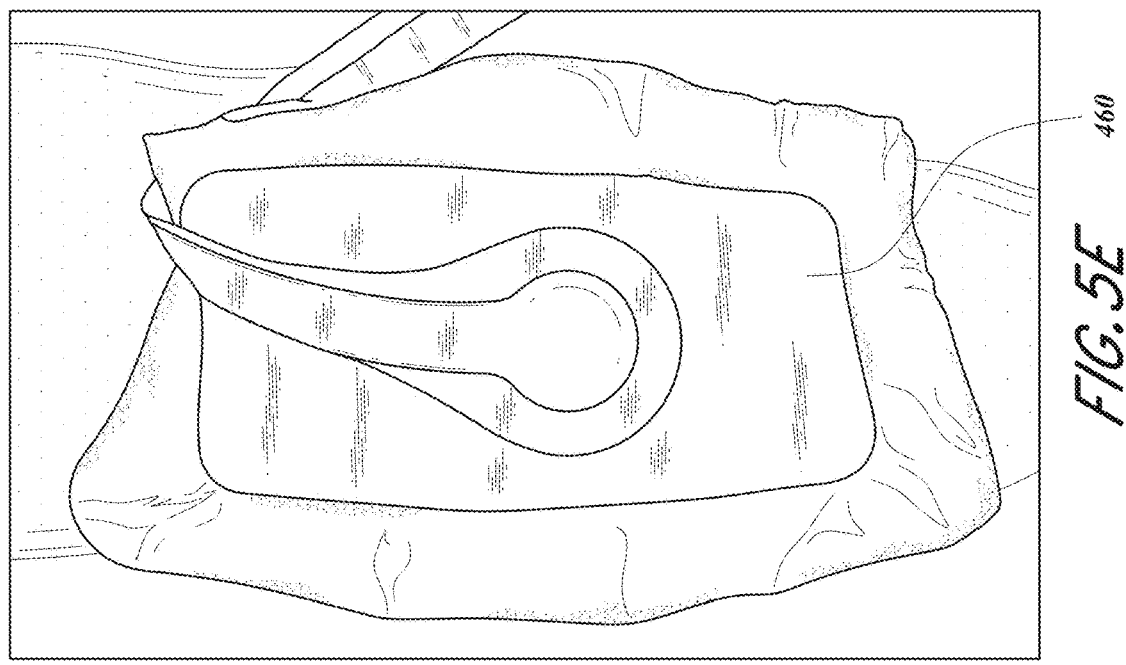

FIG. 5D-5F illustrate embodiments of the wound dressing after negative pressure has been applied. As illustrated in FIG. 5D-5F, the lower wound dressing components 450 are sucked down and conformed to the body portion and the upper wound dressing components 460 are folded and creased. In some embodiments, the upper wound dressing components 460 can be folded and sucked down in a manner similar to the shape and movement of an anemone. For example, as negative pressure is applied, the upper wound dressing components can be sucked inward and down toward the connection point in the apertures in the intermediate drape and first backing layer. The upper wound dressing components 460 can fold inward from a center portion and can fold in on itself as the edges are pushed in and up as shown in FIGS. 5D-5F. In some embodiments, the second backing layer 420 and/or the intermediate drape 422 can be flexible enough to not restrict movement or bending of the absorbent components as it is sucked in, folded, and/or creased. In some embodiments, the second backing layer 420 and/or the intermediate drape 422 can have additional material so as not to restrict movement of bending of the absorbent components while being sucked in, folded, and/or creased.

FIG. 5G illustrates an embodiment of a negative pressure wound treatment system employing lower wound dressing components including a foam layer capable of conforming to a patient and upper wound dressing components capable of absorbing and storing wound exudate. In some embodiments, as illustrated in FIG. 5G, the foam or spacer layer 424 of the lower wound dressing components can have a larger diameter and extend outward beyond the perimeter of the absorbent material 421. As illustrated in FIG. 5G, the foam or lower space layer 424 can have a perimeter size that is bigger than the absorbent layer 421 and/or the spacer layer of the absorbent dressing components on top of it. In some embodiments, this can guard against pad edge imprinting. In some embodiments, the lower spacer layer 424 can be about 5 mm bigger all around than the absorbent layer 421.

Figure 6A:
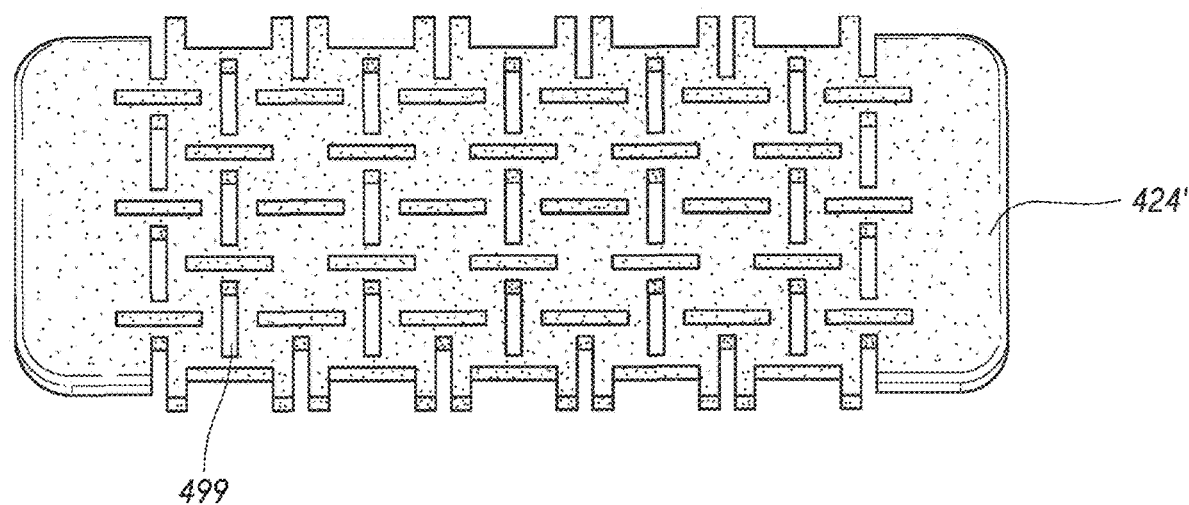

In some embodiments, the lower spacer layer or foam layer 424' can include slits or cut outs 499 in the foam material as illustrated in FIG. 6A-6B. The slit or cut out modification to the foam or spacer material 424' can provide a further increase in the materials ability to conform to a contoured shape or body portion. FIGS. 6A-6B illustrates embodiments of foam layer 424' for use in a negative pressure wound treatment system. When utilizing the foam slits or cut outs 499, the foam material can be stiffer and the slits will still allow the contouring of the foam or spacer layer material 424' to the body of the patient. The slits or cut outs 499 can include one or more slits or cut outs that are horizontal (extend parallel to a length of the foam or spacer material 424'). The slits or cut outs 499 can include one or more slits or cut outs that are vertical (extend perpendicular to a length of the foam or spacer material 424'). In some embodiments, the slits or cut outs 499 can include one or more slits or cut outs that are horizontal and one or more slits or cut outs that are vertical as shown in FIGS. 6A-6B. By providing slits or cut outs that extend in two different directions, the foam or spacer material 424' can conform and wrap around a contoured body region of a patient along both the length and width of the foam or spacer material 424'. In some embodiments, the slits or cut outs 499 can be distributed throughout the foam or spacer material 424'. In other embodiments, the slits or cut outs can be localized to a portion of the foam or spacer material 424'. For example, the slits or cut outs can be only in a center portion and/or only on an edge portion. In some embodiments, the slits or cut outs 499 can be provided in a pattern and/or evenly distributed on the foam or spacer material 424'. In some embodiments, the slits or cut outs 499 can be randomly distributed or provided on the foam or spacer layer 424'.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A negative pressure wound therapy apparatus, comprising:
   a wound dressing comprising a first dressing portion and a second dressing portion overlying the first dressing portion, the first dressing portion comprising:
- a tissue contact layer configured to be positioned in contact with a wound and/or skin surrounding a wound, wherein the tissue contact layer comprises a first border portion at a perimeter of the tissue contact layer;
- a first spacer layer; and
- a first backing layer comprising a first aperture, wherein the first backing layer comprises a second border portion at a perimeter of the first backing layer, wherein the spacer layer is positioned between the tissue contact layer and the first backing layer and the first border portion of the tissue contact layer is directly bonded to the second border portion of the first backing layer; and the second dressing portion comprising:
- an intermediate drape comprising a second aperture, wherein the intermediate drape comprises a third border portion at a perimeter of the intermediate drape;
- an absorbent layer, and
- a second backing layer comprising a fourth border portion at a perimeter of the second backing layer, wherein the absorbent layer is positioned between the intermediate drape and the second backing layer and the third border portion of the intermediate drape is directly bonded to the fourth border portion of the second backing layer; and wherein the second dressing portion is attached to the first dressing portion such that the first aperture and the second aperture are fluidly connected, and wherein the second border portion of the first backing layer is unattached and not bonded to the third border portion of the intermediate drape.

2. The negative pressure wound therapy apparatus of claim 1, further comprising a suction port attached to the second backing layer over a third aperture in the second backing layer.

3. The negative pressure wound therapy apparatus of claim 2, further comprising a filter configured to prevent or inhibit liquid from entering the suction port.

4. The negative pressure wound therapy apparatus of claim 2, further comprising a negative pressure source configured to apply negative pressure through the third aperture in the second backing layer, wherein the first, second, and third apertures are in fluid communication with each other and are configured to provide fluid communication between the negative pressure source and the wound.

5. The negative pressure wound therapy apparatus of claim 1, wherein the first spacer layer comprises foam.

6. The negative pressure wound therapy apparatus of claim 1, wherein the absorbent layer comprises superabsorbent material.

7. The negative pressure wound therapy apparatus of claim 1, further comprising a second spacer layer, wherein the second spacer layer is positioned between the absorbent layer and the intermediate drape.

8. The negative pressure wound therapy apparatus of claim 7, wherein the second spacer layer comprises a 3D fabric.

9. The negative pressure wound therapy apparatus of claim 1, wherein the first backing layer comprises a flexible material or additional material configured to allow the first backing material to bend.

10. The negative pressure wound therapy apparatus of claim 1, wherein the first spacer layer comprises a plurality of slits.

11. The negative pressure wound therapy apparatus of claim 1, further comprising a through-hole extending through the absorbent layer.

12. The negative pressure wound therapy apparatus of claim 11, wherein the through-hole is aligned underneath a suction port attached to the second backing layer.

13. The negative pressure wound therapy apparatus of claim 1, wherein the second backing layer comprises a moisture vapor permeable material.

14. The negative pressure wound therapy apparatus of claim 1, wherein the tissue contact layer, the first backing layer, the intermediate drape and the second backing layer all have substantially the same perimeter size and shape.

15. The negative pressure wound therapy apparatus of claim 1, wherein the first backing layer is configured to be attached to the intermediate drape at an area around the first aperture and an area around the second aperture.

16. The negative pressure wound therapy apparatus of claim 1, wherein the first spacer layer has a smaller perimeter size than the tissue contact layer and the first backing layer.

17. The negative pressure wound therapy apparatus of claim 1, wherein the first spacer layer has a rectangular, rounded rectangular, racetrack, oval, circular, triangular, or irregular shape.

18. The negative pressure wound therapy apparatus of claim 2, wherein the third aperture in the second backing layer is located at a central region of the second backing layer.

19. The negative pressure wound therapy apparatus of claim 2, wherein the third aperture in the second backing layer is located at an edge region of the second backing layer.

20. The negative pressure wound therapy apparatus of claim 2, wherein the third aperture in the second backing layer is located at a corner of the second backing layer.

21. The negative pressure wound therapy apparatus of claim 1, wherein the tissue contact layer extends across an entire area below the first backing layer.

22. The negative pressure wound therapy apparatus of claim 1, wherein the tissue contact layer comprises apertures, pores, or perforations to enable fluid to flow through the tissue contact layer.

23. A method of treating a wound with a negative pressure wound therapy apparatus, comprising:
positioning a wound dressing over the wound, the wound dressing comprising:
- a first portion and a second portion, the first portion comprising:
  - a tissue contact layer configured to be positioned in contact with a wound and/or skin surrounding a wound, wherein the tissue contact layer comprises a first border portion at a perimeter of the tissue contact layer;
  - a first spacer layer; and
  - a first backing layer comprising a first aperture, wherein the first backing layer comprises a second border portion at a perimeter of the first backing layer, wherein the spacer layer is positioned between the tissue contact layer and the first backing layer and the first border portion of the tissue contact layer is directly bonded to the second border portion of the first backing layer; and the second dressing portion comprising:
- an intermediate drape comprising a second aperture, wherein the intermediate drape comprises a third border portion at a perimeter of the intermediate drape;
- an absorbent layer, and
- a second backing layer comprising a fourth border portion at a perimeter of the second backing layer, wherein the absorbent layer is positioned between the intermediate drape and the second backing layer and the third border portion of the intermediate drape is directly bonded to the fourth border portion of the second backing layer;

wherein the second dressing portion is attached to the first dressing portion such that the first aperture and the second aperture are fluidly connected, and wherein the second border portion of the first backing layer is unattached and not bonded to the third border portion of the intermediate drape; and applying negative pressure through a third aperture in the second backing layer, wherein the first, second, and third apertures provide fluid communication between a source of negative pressure and the wound.

24. The negative pressure wound therapy apparatus of claim 1, wherein the first dressing portion and the second dressing portion are configured to allow the first backing layer to conform to the wound and/or skin surrounding the wound with the first dressing portion and configured to allow the intermediate drape to fold or bend with the second dressing portion independent of the first dressing portion and the first backing layer as the second border portion of the first backing layer is unattached to the third border portion of the intermediate drape.

25. The method of claim 23, wherein the first dressing portion and the second dressing portion are configured to allow the first backing layer to conform to the wound and/or skin surrounding the wound with the first dressing portion and configured to allow the intermediate drape to fold or bend with the second dressing portion independent of the first dressing portion and the first backing layer as the second border portion of the first backing layer is unattached to the third border portion of the intermediate drape.

* * * * *